US012611101B2

(12) United States Patent
    Sacks

(10) Patent No.:     US 12,611,101 B2
(45) Date of Patent:        Apr. 28, 2026

(54) GONIOSCOPIC LASER SURGERY

(71) Applicant: Belkin Vision Ltd., Yavne (IL)

(72) Inventor: Zachary Sacks, Modiin (IL)

(73) Assignee: BELKIN VISION LTD., Yavne (IL)

( * ) Notice:    Subject to any disclaimer, the term of this patent is extended or adjusted under 35 U.S.C. 154(b) by 305 days.

(21) Appl. No.: 18/398,184

(22) Filed:    Dec. 28, 2023

(65)              Prior Publication Data

US 2024/0122471 A1        Apr. 18, 2024

Related U.S. Application Data

(63) Continuation-in-part    of    application    No. PCT/IB2023/060104, filed on Oct. 9, 2023.
    (Continued)

(51) Int. Cl.
    *A61B 3/117*              (2006.01)
    *A61B 3/00*              (2006.01)
    (Continued)

(52) U.S. Cl.
    CPC ............ *A61B 3/117* (2013.01); *A61B 3/0083* (2013.01); *A61B 3/102* (2013.01); *A61B 3/135* (2013.01)

(58) Field of Classification Search
    CPC ....... A61B 3/117; A61B 3/0083; A61B 3/102; A61B 3/135; G06V 40/19; A61F 9/009;
    (Continued)

(56)              References Cited

U.S. PATENT DOCUMENTS 2,635,502 A      4/1953    Richards
3,594,072 A      7/1971    Feather
        (Continued)

FOREIGN PATENT DOCUMENTS

AU          2011379044 B2      4/2013
AU          2015210430 A1      9/2015
            (Continued)

OTHER PUBLICATIONS

Vogel et al., "Optical properties of human sclera, and their consequences for transscleral laser applications.", Lasers in Surgery and Medicine , vol. 11, pp. 331-340, year 1991.
            (Continued)

*Primary Examiner* — Mohammed A Hasan
(74) *Attorney, Agent, or Firm* — Sanders IP Law

(57)              ABSTRACT

An apparatus for medical treatment includes a gonioscope having a distal face for placement in proximity to a patient's eye, a proximal face opposite the distal face, and multiple facets between the distal and proximal faces. The apparatus also includes a laser to generate a beam, a scanner to direct the beam through the proximal face of the gonioscope to reflect from a facet into an anterior chamber of the eye, at least one slit lamp to project sheets of light into the eye through the gonioscope, a camera to capture, through the gonioscope, an image of an illumination pattern cast on the eye by the sheet of light. A processor processes the image so as to identify a location of an anatomical structure in the eye, selects targets in the eye based on the identified location, and controls the scanner so that the beam impinges on the targets.

34 Claims, 10 Drawing Sheets

Related U.S. Application Data

(60) Provisional application No. 63/414,919, filed on Oct. 11, 2022.

(51) Int. Cl.
*A61B 3/10* (2006.01)
*A61B 3/135* (2006.01)

(58) Field of Classification Search
CPC .. A61F 2009/00868; A61F 2009/00891; A61F 9/00821
USPC ......................................................... 351/206
See application file for complete search history.

(56) References Cited

U.S. PATENT DOCUMENTS

| | | | |
|---|---|---|---|
| 4,587,257 A | 5/1986 | DeSantis et al. |
| 4,641,349 A | 2/1987 | Flom et al. |
| 4,718,418 A | 1/1988 | L'Esperance |
| 4,848,894 A | 7/1989 | Buser et al. |
| 4,941,093 A | 7/1990 | Marshall et al. |
| 4,966,452 A | 10/1990 | Shields et al. |
| 5,049,147 A | 9/1991 | Danon |
| 5,123,902 A | 6/1992 | Muller et al. |
| 5,141,506 A | 8/1992 | York |
| 5,151,909 A | 9/1992 | Davenport et al. |
| 5,152,760 A | 10/1992 | Latina |
| 5,370,641 A | 12/1994 | O'Donnell, Jr. |
| 5,422,899 A | 6/1995 | Freiberg et al. |
| 5,479,222 A | 12/1995 | Volk et al. |
| 5,537,164 A | 7/1996 | Smith |
| 5,549,596 A | 8/1996 | Latina |
| 5,598,007 A | 1/1997 | Bunce et al. |
| 5,786,883 A | 7/1998 | Miller et al. |
| 5,865,830 A | 2/1999 | Parel et al. |
| 5,982,789 A | 11/1999 | Marshall et al. |
| 6,027,216 A | 2/2000 | Guyton et al. |
| 6,030,376 A | 2/2000 | Arashima et al. |
| 6,033,396 A | 3/2000 | Huang et al. |
| 6,059,772 A | 5/2000 | Hsia et al. |
| 6,090,100 A | 7/2000 | Hohla |
| 6,096,029 A | 8/2000 | O'Donnell, Jr. |
| 6,099,521 A | 8/2000 | Shadduck |
| 6,099,522 A | 8/2000 | Knopp et al. |
| 6,146,375 A | 11/2000 | Juhasz et al. |
| 6,159,202 A | 12/2000 | Sumiya et al. |
| 6,210,399 B1 | 4/2001 | Parel et al. |
| 6,258,082 B1 | 7/2001 | Lin |
| 6,263,879 B1 | 7/2001 | Lin |
| 6,267,752 B1 | 7/2001 | Svetliza |
| 6,267,756 B1 | 7/2001 | Feuerstein et al. |
| 6,286,960 B1 | 9/2001 | Tomita |
| 6,319,274 B1 | 11/2001 | Shadduck |
| 6,325,792 B1 | 12/2001 | Swinger et al. |
| 6,414,980 B1 | 7/2002 | Wang et al. |
| 6,454,763 B1 | 9/2002 | Motter et al. |
| 6,514,241 B1 | 2/2003 | Hsia et al. |
| 6,530,916 B1 | 3/2003 | Shimmick |
| 6,569,104 B2 | 5/2003 | Ono et al. |
| 6,585,723 B1 | 7/2003 | Sumiya |
| 6,673,062 B2 | 1/2004 | Yee et al. |
| 6,676,655 B2 | 1/2004 | McDaniel |
| 6,685,317 B2 | 2/2004 | Su et al. |
| 6,698,886 B2 | 3/2004 | Pollack et al. |
| 6,736,806 B2 | 5/2004 | Ruiz et al. |
| 6,761,713 B2 | 7/2004 | Teichmann |
| 6,899,707 B2 | 5/2005 | Scholler et al. |
| 6,942,656 B2 | 9/2005 | Pawlowski et al. |
| 6,948,815 B2 | 9/2005 | Neuberger |
| 6,979,328 B2 | 12/2005 | Baerveldt et al. |
| 7,027,233 B2 | 4/2006 | Goldstein et al. |
| 7,252,661 B2 | 8/2007 | Nguyen et al. |
| 7,282,046 B2 | 10/2007 | Simon |
| 7,353,829 B1 | 4/2008 | Wachter et al. |
| 7,371,230 B2 | 5/2008 | Webb et al. |
| 7,693,259 B2 | 4/2010 | Gertner |
| 7,792,249 B2 | 9/2010 | Gertner et al. |
| 8,004,764 B2 | 8/2011 | Artsyukhovich et al. |
| 8,048,065 B2 | 11/2011 | Grecu et al. |
| 8,109,635 B2 | 2/2012 | Allon et al. |
| 8,160,113 B2 | 4/2012 | Adams et al. |
| 8,403,921 B2 | 3/2013 | Palankar et al. |
| 8,442,185 B2 | 5/2013 | Gertner et al. |
| 8,465,478 B2 | 6/2013 | Frey et al. |
| 8,475,433 B2 | 7/2013 | Mrochen et al. |
| 8,545,020 B2 | 10/2013 | Liesfeld et al. |
| 8,568,393 B2 | 10/2013 | Palanker |
| 8,630,388 B2 | 1/2014 | Gertner et al. |
| 8,679,100 B2 | 3/2014 | Raksi et al. |
| 8,708,491 B2 | 4/2014 | Frey et al. |
| 8,709,029 B2 | 4/2014 | Griffis, III et al. |
| 8,771,261 B2 | 7/2014 | Andersen et al. |
| 8,811,657 B2 | 8/2014 | Teiwes et al. |
| 8,845,625 B2 | 9/2014 | Angeley et al. |
| 8,903,468 B2 | 12/2014 | Peyman |
| 8,920,407 B2 | 12/2014 | Raksi et al. |
| 8,939,965 B2 | 1/2015 | Liesfeld et al. |
| 8,968,279 B2 | 3/2015 | Arnoldussen |
| 8,995,618 B2 | 3/2015 | Gertner |
| 9,055,896 B2 | 6/2015 | Amthor et al. |
| 9,192,780 B2 | 11/2015 | McDaniel |
| 9,220,407 B2 | 12/2015 | Yam et al. |
| 9,351,878 B2 | 5/2016 | Muehlhoff et al. |
| 9,480,599 B2 | 11/2016 | Degani et al. |
| 9,495,743 B2 | 11/2016 | Angeley et al. |
| 9,504,609 B2 | 11/2016 | Kurtz |
| 9,532,712 B2 | 1/2017 | Liesfeld et al. |
| 9,622,911 B2 | 4/2017 | Rubinfeld et al. |
| 9,782,232 B1 | 10/2017 | Papac |
| 9,849,032 B2 | 12/2017 | Schuele et al. |
| 9,849,034 B2 | 12/2017 | Artsyukhovich et al. |
| 9,877,633 B2 | 1/2018 | Zhao et al. |
| 9,889,043 B2 | 2/2018 | Frey et al. |
| 9,968,483 B2 | 5/2018 | Takeda et al. |
| 10,022,457 B2 | 7/2018 | Peyman |
| 10,064,757 B2 | 9/2018 | Berlin |
| 10,143,590 B2 | 12/2018 | Dick et al. |
| 10,244,991 B2 | 4/2019 | Shademan et al. |
| 10,258,507 B2 | 4/2019 | Gonzalez et al. |
| 10,278,865 B2 | 5/2019 | Luttrull et al. |
| 10,299,961 B2 | 5/2019 | Luttrull et al. |
| 10,363,169 B2 | 7/2019 | Belkin et al. |
| 10,441,465 B2 | 10/2019 | Hart et al. |
| 10,449,091 B2 | 10/2019 | Angeley et al. |
| 10,456,209 B2 | 10/2019 | Peyman |
| 10,478,342 B2 | 11/2019 | Dick et al. |
| 10,524,656 B2 | 1/2020 | Wiltberger et al. |
| 10,617,564 B1 | 4/2020 | Andersen et al. |
| 10,684,449 B2 | 6/2020 | Curatu et al. |
| 10,702,416 B2 | 7/2020 | Belkin et al. |
| 10,849,789 B2 | 12/2020 | Dewey et al. |
| 10,925,768 B2 | 2/2021 | Charles |
| 2001/0027314 A1 | 10/2001 | Peyman |
| 2002/0013572 A1 | 1/2002 | Berlin |
| 2002/0013573 A1 | 1/2002 | Telfair et al. |
| 2002/0026179 A1 | 2/2002 | Toh |
| 2003/0179344 A1 | 9/2003 | Van de Velde |
| 2003/0225398 A1 | 12/2003 | Zepkin et al. |
| 2004/0039378 A1 | 2/2004 | Lin |
| 2004/0059321 A1 | 3/2004 | Knopp et al. |
| 2004/0196431 A1 | 10/2004 | Farberov |
| 2005/0096639 A1 | 5/2005 | Slatkine et al. |
| 2005/0107774 A1 | 5/2005 | Lin |
| 2005/0185138 A1 | 8/2005 | Wong et al. |
| 2005/0197655 A1 | 9/2005 | Telfair et al. |
| 2005/0254009 A1 | 11/2005 | Baker et al. |
| 2005/0286019 A1 | 12/2005 | Wiltberger et al. |
| 2005/0288745 A1* | 12/2005 | Andersen ............ A61F 9/00781 607/86 |
| 2006/0100677 A1 | 5/2006 | Blumenkranz et al. |
| 2006/0176913 A1 | 8/2006 | Souhaite et al. |
| 2006/0195076 A1 | 8/2006 | Blumenkranz et al. |
| 2006/0224147 A1 | 10/2006 | Abe et al. |
| 2006/0265030 A1 | 11/2006 | McDaniel |

(56) References Cited

U.S. PATENT DOCUMENTS

| 2007/0081166 A1 | 4/2007 | Brown et al. |
| 2007/0129709 A1 | 6/2007 | Andersen et al. |
| 2007/0159600 A1 | 7/2007 | Gil et al. |
| 2007/0213693 A1 | 9/2007 | Plunkett |
| 2008/0027418 A1 | 1/2008 | Berry |
| 2008/0089481 A1 | 4/2008 | Gertner |
| 2008/0108934 A1 | 5/2008 | Berlin et al. |
| 2008/0161781 A1 | 7/2008 | McArdle et al. |
| 2008/0167642 A1 | 7/2008 | Palanker et al. |
| 2008/0204658 A1 | 8/2008 | Van Saarloos |
| 2008/0215039 A1* | 9/2008 | Slatkine ............... A61M 5/425 |
| | | 606/9 |
| 2008/0234667 A1 | 9/2008 | Lang et al. |
| 2008/0255546 A1 | 10/2008 | Orbachevski |
| 2009/0137993 A1 | 5/2009 | Kurtz |
| 2009/0157062 A1 | 6/2009 | Hauger et al. |
| 2009/0247997 A1 | 10/2009 | Watanabe et al. |
| 2010/0002837 A1 | 1/2010 | Gertner et al. |
| 2010/0057059 A1 | 3/2010 | Makino |
| 2010/0076419 A1 | 3/2010 | Chew et al. |
| 2010/0142767 A1 | 6/2010 | Fleming |
| 2010/0324543 A1 | 12/2010 | Kurtz et al. |
| 2011/0144627 A1 | 6/2011 | Smith et al. |
| 2011/0172649 A1 | 7/2011 | Schuele et al. |
| 2011/0190741 A1 | 8/2011 | Deisinger et al. |
| 2012/0016349 A1 | 1/2012 | Brownell |
| 2012/0050308 A1 | 3/2012 | Nakano et al. |
| 2012/0083772 A1 | 4/2012 | Rubinfeld et al. |
| 2012/0089134 A1 | 4/2012 | Horvath et al. |
| 2012/0259321 A1 | 10/2012 | Vera et al. |
| 2012/0283557 A1 | 11/2012 | Berlin |
| 2013/0103011 A1 | 4/2013 | Grant et al. |
| 2013/0123761 A1 | 5/2013 | Belkin et al. |
| 2013/0158530 A1 | 6/2013 | Goldshleger et al. |
| 2013/0204236 A1 | 8/2013 | Awdeh |
| 2013/0218145 A1 | 8/2013 | Belkin et al. |
| 2013/0289450 A1 | 10/2013 | Homer |
| 2013/0317570 A1 | 11/2013 | Luttrull et al. |
| 2014/0094785 A1 | 4/2014 | Charles |
| 2014/0114297 A1 | 4/2014 | Woodley et al. |
| 2014/0128731 A1 | 5/2014 | Gonzalez et al. |
| 2014/0128851 A1 | 5/2014 | Wysopal |
| 2014/0128852 A1 | 5/2014 | Gooding et al. |
| 2014/0135747 A1 | 5/2014 | Donitzky et al. |
| 2014/0135753 A1 | 5/2014 | Feklistov et al. |
| 2014/0276681 A1 | 9/2014 | Schuele et al. |
| 2014/0307077 A1 | 10/2014 | Prabhakar |
| 2015/0164635 A1 | 6/2015 | Renke |
| 2015/0190276 A1 | 7/2015 | Ha et al. |
| 2015/0223683 A1 | 8/2015 | Davidovics et al. |
| 2015/0266706 A1 | 9/2015 | Hashimoto |
| 2015/0272782 A1 | 10/2015 | Schuele et al. |
| 2015/0313759 A1 | 11/2015 | Vera et al. |
| 2015/0366706 A1 | 12/2015 | Belkin et al. |
| 2016/0008169 A1 | 1/2016 | Yu |
| 2016/0008172 A1 | 1/2016 | Kahook |
| 2016/0067035 A1 | 3/2016 | Gontijo et al. |
| 2016/0067087 A1 | 3/2016 | Tedford et al. |
| 2016/0089232 A1 | 3/2016 | DeBoer et al. |
| 2016/0089269 A1 | 3/2016 | Horvath et al. |
| 2016/0095752 A1 | 4/2016 | Srinivasan et al. |
| 2016/0113816 A1 | 4/2016 | Herekar et al. |
| 2016/0346126 A1 | 12/2016 | Luttrull et al. |
| 2016/0354241 A1 | 12/2016 | Mordaunt et al. |
| 2016/0367399 A1 | 12/2016 | Goldshleger et al. |
| 2017/0000647 A1 | 1/2017 | Schuele et al. |
| 2017/0038284 A1 | 2/2017 | Nemati |
| 2017/0087014 A1 | 3/2017 | Potter, Jr. et al. |
| 2017/0127938 A1 | 5/2017 | Izatt et al. |
| 2017/0184875 A1 | 6/2017 | Newman |
| 2017/0246033 A1 | 8/2017 | Bor et al. |
| 2017/0340483 A1 | 11/2017 | Rill et al. |
| 2017/0360604 A1 | 12/2017 | Bach et al. |
| 2018/0085257 A1 | 3/2018 | Horvath et al. |
| 2018/0104477 A1 | 4/2018 | Kurtz et al. |
| 2018/0125708 A1 | 5/2018 | Bohme et al. |
| 2018/0168737 A1 | 6/2018 | Ren et al. |
| 2018/0207029 A1 | 7/2018 | Herekar et al. |
| 2018/0214305 A1 | 8/2018 | Schuele et al. |
| 2018/0221199 A1 | 8/2018 | Heacock |
| 2018/0235462 A1 | 8/2018 | Gooi et al. |
| 2018/0344527 A1 | 12/2018 | Palanker et al. |
| 2019/0078073 A1 | 3/2019 | Streeter et al. |
| 2019/0099291 A1 | 4/2019 | Herekar et al. |
| 2019/0105200 A1 | 4/2019 | Hipsley |
| 2019/0105519 A1 | 4/2019 | Herekar et al. |
| 2019/0117459 A1 | 4/2019 | Berlin |
| 2019/0142636 A1 | 5/2019 | Tedford et al. |
| 2019/0151146 A1 | 5/2019 | Kim |
| 2019/0247225 A1 | 8/2019 | Stobrawa et al. |
| 2019/0269554 A1 | 9/2019 | Goldshleger et al. |
| 2019/0343680 A1 | 11/2019 | Belkin et al. |
| 2019/0344076 A1 | 11/2019 | Irazoqui et al. |
| 2019/0358085 A1 | 11/2019 | Fu et al. |
| 2020/0038245 A1 | 2/2020 | Hart et al. |
| 2020/0078216 A1 | 3/2020 | Raksi |
| 2020/0093639 A1 | 3/2020 | McCall, Jr. |
| 2020/0107724 A1 | 4/2020 | Wiltberger et al. |
| 2020/0146887 A1 | 5/2020 | Horvath et al. |
| 2020/0306080 A1 | 10/2020 | Herekar et al. |
| 2020/0345546 A1* | 11/2020 | Belkin ............... A61F 9/00817 |
| 2020/0352785 A1* | 11/2020 | Holland ............. A61F 9/00781 |
| 2020/0360187 A1 | 11/2020 | Schuele et al. |
| 2020/0379216 A1 | 12/2020 | Curatu et al. |
| 2021/0113373 A1 | 4/2021 | Sacks et al. |
| 2021/0267800 A1 | 9/2021 | Sacks et al. |
| 2021/0338484 A1 | 11/2021 | Hipsley |
| 2021/0393438 A1 | 12/2021 | Degani et al. |
| 2022/0031503 A1 | 2/2022 | Dorin et al. |
| 2022/0249861 A1 | 8/2022 | Belkin et al. |
| 2023/0201034 A1 | 6/2023 | Sacks et al. |
| 2023/0201037 A1 | 6/2023 | Barrett et al. |
| 2023/0226372 A1 | 7/2023 | Herekar et al. |
| 2023/0329911 A1 | 10/2023 | Sacks et al. |

FOREIGN PATENT DOCUMENTS

| AU | 2015315113 B2 | 3/2016 |
| CA | 2640203 A1 | 8/2007 |
| CN | 1579351 A | 2/2005 |
| CN | 101411607 A | 4/2009 |
| CN | 201537172 U | 8/2010 |
| CN | 102193182 A | 9/2011 |
| CN | 105138996 A | 12/2015 |
| CN | 205698218 U | 11/2016 |
| CN | 108024870 A | 1/2022 |
| DE | 202016006265 U1 | 3/2017 |
| DE | 102021204066 A1 | 10/2022 |
| EP | 0224322 A1 | 6/1987 |
| EP | 0651982 A1 | 5/1995 |
| EP | 0689811 A1 | 1/1996 |
| EP | 1602321 A1 | 12/2005 |
| EP | 2301421 A1 | 3/2011 |
| EP | 2301424 B1 | 3/2011 |
| EP | 2301425 B1 | 3/2011 |
| EP | 2602005 A1 | 6/2013 |
| EP | 1856774 B1 | 6/2016 |
| EP | 2695016 B1 | 3/2017 |
| EP | 2992931 B1 | 8/2017 |
| EP | 2391318 B1 | 12/2017 |
| EP | 3329839 A1 | 6/2018 |
| EP | 2729099 B1 | 11/2019 |
| EP | 3191040 B1 | 7/2020 |
| EP | 3517081 B1 | 11/2020 |
| EP | 2854729 B1 | 3/2021 |
| FR | 2655837 A1 | 6/1991 |
| JP | 2007151739 A | 6/2007 |
| JP | 2010506689 A | 3/2010 |
| JP | 2010148635 A | 7/2010 |
| JP | 2016013255 A | 1/2016 |
| JP | 2016507321 A | 3/2016 |
| JP | 2017506573 A | 3/2017 |
| JP | 2017506944 A | 3/2017 |
| JP | 2018051210 A | 4/2018 |

(56) References Cited

FOREIGN PATENT DOCUMENTS

| KR | 20180106113 A | 10/2018 |
|---|---|---|
| KR | 20190022216 A | 3/2019 |
| RU | 2499582 C1 | 11/2013 |
| RU | 2553507 C1 | 6/2015 |
| WO | 9216259 A1 | 10/1992 |
| WO | 1993012727 A1 | 7/1993 |
| WO | 9316631 A1 | 9/1993 |
| WO | 9412092 A1 | 6/1994 |
| WO | 9416425 A1 | 7/1994 |
| WO | 9515134 A1 | 6/1995 |
| WO | 1998022016 A2 | 5/1998 |
| WO | 1998048746 A1 | 11/1998 |
| WO | 9918868 A1 | 4/1999 |
| WO | 0195842 A1 | 12/2001 |
| WO | 02064031 A2 | 8/2002 |
| WO | 02087442 A1 | 11/2002 |
| WO | 2014018104 A1 | 1/2004 |
| WO | 2004027487 A1 | 4/2004 |
| WO | 2006119349 A2 | 11/2006 |
| WO | 2006119584 A1 | 11/2006 |
| WO | 2006128038 A2 | 11/2006 |
| WO | 2007103349 A2 | 9/2007 |
| WO | 2008112236 A1 | 9/2008 |
| WO | 2008118198 A2 | 10/2008 |
| WO | 2010094353 A1 | 8/2010 |
| WO | 2010113193 A1 | 10/2010 |
| WO | 2011017002 A2 | 2/2011 |
| WO | 2011163508 A2 | 6/2011 |
| WO | 2011085274 A1 | 7/2011 |
| WO | 2011151812 A1 | 12/2011 |
| WO | 2013004255 A1 | 1/2013 |
| WO | 2013035091 A1 | 3/2013 |
| WO | 2013059481 A1 | 4/2013 |
| WO | 2013059564 A1 | 4/2013 |
| WO | 2013122711 A1 | 8/2013 |
| WO | 2013165689 A1 | 11/2013 |
| WO | 2014025862 A1 | 2/2014 |
| WO | 2014132162 A1 | 9/2014 |
| WO | 2014191031 A1 | 12/2014 |
| WO | 2015069197 A1 | 5/2015 |
| WO | 2015119888 A1 | 8/2015 |
| WO | 2015130821 A2 | 9/2015 |
| WO | 2015131135 A1 | 9/2015 |
| WO | 2016018864 A1 | 2/2016 |
| WO | 2016058931 A2 | 4/2016 |
| WO | 2016156760 A1 | 10/2016 |
| WO | 2016187436 A1 | 11/2016 |
| WO | 2016207739 A1 | 12/2016 |
| WO | 2017023296 A1 | 2/2017 |
| WO | 2017031570 A1 | 3/2017 |
| WO | 2017069819 A1 | 4/2017 |
| WO | 2018005796 A1 | 1/2018 |
| WO | 2018021780 A1 | 2/2018 |
| WO | 2018049246 A1 | 3/2018 |
| WO | 2018152020 A1 | 8/2018 |
| WO | 2018232397 A1 | 12/2018 |
| WO | 2019109125 A1 | 6/2019 |
| WO | 2020008323 A1 | 1/2020 |
| WO | 2020012841 A1 | 1/2020 |
| WO | 2020018242 A1 | 1/2020 |
| WO | 2020018436 A1 | 1/2020 |
| WO | 2020050308 A1 | 3/2020 |
| WO | 202093060 A2 | 5/2020 |
| WO | 2020089737 A1 | 5/2020 |
| WO | 2020093060 A2 | 5/2020 |
| WO | 2020183342 A1 | 9/2020 |
| WO | 2021026538 A1 | 2/2021 |
| WO | 2021048723 A1 | 3/2021 |
| WO | 2021155445 A1 | 8/2021 |
| WO | 2021170664 A1 | 9/2021 |
| WO | 2022223690 A1 | 10/2022 |

OTHER PUBLICATIONS

Geffen et al., "Transscleral Selective Laser Trabeculoplasty Without a Gonioscopy Lens", Journal of Glaucoma, Inc, vol. 26, No. 3, pp. 201-207, Mar. 2017.

Das et al., "Sclera Recognition—A Survey", 2nd IAPR Asian Conference on Pattern Recognition, pp. 1-5, year 2013.

Kaya et al., "Designing a Pattern Stabilization Method Using Scleral Blood Vessels for Laser Eye Surgery", International Conference on Pattern Recognition, pp. 698-701, Istanbul, Turkey, Aug. 23-26, 2010.

Barkana et al., "Selective Laser Trabeculoplasty", Survey of Ophthalmology, vol. 52, No. 6, pp. 634-653, year 2007.

Arany, "Photobiomodulation therapy: Easy to do, but difficult to get right", LaserFocusWorld, pp. 1-6, Jul. 31, 2019 downloaded from www.laserfocusworld.com/lasers-sources/article/14037967/photobiomodulation-therapyeasy-to-do-but-difficult-to-get-right, pp. 22-24, year 2019.

Borzabadi-Farahani, "Effect of low-level laser irradiation on proliferation of human dental mesenchymal stem cells; a systemic review", Journal of Photochemistry and Photobiology B: Biology, vol. 162, pp. 577-582, Sep. 2016.

Acott et al., "Trabecular Repopulation by Anterior Trabecular Meshwork Cells After Laser Trabeculoplasty", American Journal of Ophthalmology, vol. 107, issue 1, pp. 1-6, Jan. 1989.

Cao et al., "Peripheral Iridotomy," Medscape 25, pp. 1-12, Jun. 15, 2020.

Husain, "Laser Peripheral Iridotomy—Practical Points", YouTube presentation, p. 1, Sep. 28, 2016, downloaded from https://www.youtube.com/watch?= Azxzsv31yls.

Ivandic et al., "Early Diagnosis of Ocular Hypertension Using a Low-Intensity Laser Irradiation Test", Photomedicine and Laser Surgery, vol. 00, No. 00, pp. 1-5, year 2009.

Smith et al., "Light scatter from the central human cornea", Journal "Eye", issue 4, pp. 584-588, year 1990.

Turati et al., "Patterned Laser Trabeculoplasty", Ophthalmic Surgery, Lasers and Imaging , vol. 41, No. 5, pp. 538-545, year 2010.

Nozaki et al., "Patterned Laser Trabeculoplasty with Pascal streamline 577", Investigative Ophthalmology & Visual Science, vol. 54, p. 1867, Jun. 2013.

Acktar, "Magic Black Coatings", Product Information, pp. 1-6, year 2017.

Acktar, "Fractal Black Coating", Product Information, pp. 1-5, year 2017.

Cloudy Nights LLC, "Cloudy Nights—Equipment Discussions—ATM", Optics and DIY Forum, pp. 1-5, Feb. 15, 2015.

Defense Tech, "Anti-Laser Contact Lenses", Product Information, p. 1-1, Nov. 29, 2004.

IEC standard 60825-1, "Safety of Laser Products", Edition 1.2, pp. 1-122, years 2001-2008.

Laser Safety Industries, "Filter Specifications", pp. 1-5, year 2008.

Thorlabs, "Laser Safety Glasses", Product Information, p. 1, Nov. 3, 2014.

Surrey Nanosystems LTD, "Vantablack", Data Sheet, pp. 1-4, Mar. 1, 2016.

Danielson et al., Fixed High-Energy versus Standard Titrated Energy Settings for Selective Laser Trabeculoplasty, Journal of Glaucoma Publish Ahead of Print, Wolters Kluwer Health, Inc., pp. 1-16, year 2023.

Radcliffe et al., "Energy Dose-Response in Selective Laser Trabeculoplasty: A Review," Journal of Glaucoma, vol. 31, pp. e49-e68, year 2022.

Gazzard, "A Brief Guide to Gonioscopy," Video Clip, Optometry today, pp. 1-2, May 21, 2015, as downloaded from https://www.youtube.com/watch?v=8yTTbHWxUik.

Alward et al., "Principles of Gonioscopy," Color Atlas of Gonioscopy, American Academy of Opthalmology, pp. 1-10, Nov. 8, 2017, as downloaded from https://www.aao.org/education/disease-review/principles-of-gonioscopy.

Nolan et al., "Gonioscopy skills and techniques," Community Eye Health Journal, vol. 34, No. 112, pp. 40-42, year 2021.

Breazzano et al., "Analysis of Schwalbe's Line (Limbal Smooth Zone) by Scanning Electron Microscopy and Optical Coherence

(56)         References Cited

OTHER PUBLICATIONS

Tomography in Human Eye Bank Eyes," Journal of Ophthalmic and Vision Research, vol. 8, issue 1, pp. 9-16, Jan. 2013.

Thorlabs, Inc., "CPS520—Collimated Laser Diode Module, 520 nm, 4.5 mW, Elliptical Beam, Ø11 mm," Product Details, pp. 1-1, years 1999-2023, as downloaded from https://www.thorlabs.com/thorproduct.cfm?partnumber=CPS520.

Prophotonix, "Green Laser Modules," Product Information, pp. 1-8, year 2024, as downloaded from https://www.prophotonix.com/led-and-laser-products/laser-modules/laser-modules-color/green-laser-modules/.

Idex Helath & Science LLC, "532 nm StopLine® single-notch filter," Product Details, pp. 1-2, year 2023 as downloaded from https://www.idex-hs.com/store/product-detail/nf03_532e_25/fl-009362?cat_id=products&node=individual_optical_filters.

Brackley et al., "Lecture: Using the Slit Lamp Microscope to Visualize the Ocular Structures," Video Clip, pp. 1-2, Sep. 17, 2022, as downloaded from https://www.youtube.com/watch?v=1E-sEhy9tBo.

Bruce et al., "Zoom in on Gonioscopy," Review of Optometry, pp. 1-8, Sep. 1, 2016, as downloaded from https://www.reviewofoptometry.com/article/zoom-in-on-gonioscopy.

AU Application # 2022211843 Office Action dated Jan. 8, 2024.

JP Application # 2022508451 Office Action dated Mar. 5, 2024.

Root, "How to perform a Laser Iridotomy (Video)," pp. 1-14, year 2010, as downloaded from https://timroot.com/how-to-perform-a-laser-iridotomy-video/.

International Application # PCT/IB2023/060104 Search Report Dec. 26, 2023.

AU Application # 2021369792 Office Action dated Mar. 21, 2024.

Gazzard et al., "Selective Laser Trabeculoplasty versus Drops for Newly Diagnosed Ocular Hypertension and Glaucoma: The Light RCT," Health Technology Assessment, NHS, vol. 23, issue 31, pp. 1-132, Jun. 2019.

Kelley et al., "Stem Cells in the Trabecular Meshwork: Present and Future Promises," Experimental Eye Research, vol. 88, issue 4, pp. 747-751, Apr. 2009.

Dueker et al., "Stimulation of Cell Division by Argon and Nd:YAG Laser Trabeculoplasty in Cynomolgus Monkeys," Investigative Ophthalmology & Visual Science, vol. 31, No. 1, pp. 115-124, year 1990.

Nowell et al., "Corneal Epithelial Stem Cells and their Niche at a Glance," Cell Science at a Glance, vol. 130, issue 6, pp. 1021-1025, year 2017.

Kim et al., "Diagnosis of Corneal Limbal Stem Cell Deficiency," Current Opinion in Ophthalmology, Wolters Kluwer Health, Inc., vol. 28, No. 4, pp. 355-362, Jul. 2017.

Gonzalez et al., "Limbal Stem Cells: Identity, Developmental Origin, and Therapeutic Potential," WIREs Developmental Biology, Wiley, vol. 7, issue 2, pp. 1-23, Mar. 2018.

Sepehr, "Corneal Endothelial Cell Dysfunction: Etiologies and Management," Therapeutic Advances in Opthalmology, pp. 1-19, year 2018.

Espana et al., "Existence of Corneal Endothelial Slow-Cycling Cells," Investigative Ophthalmology & Visual Science, vol. 56, No. 6, pp. 3827-3837, Jun. 2015.

Walshe et al., "Serial Explant Culture Provides Novel Insights into the Potential Location and Phenotype of Corneal Endothelial Progenitor Cells," Experimental Eye Research, vol. 127, pp. 9-13, year 2014.

Pinnamaneni et al., "Concise Review: Stem Cells in the Corneal Stroma," Stem Cells, vol. 30, issue 6, pp. 1059-1063, year 2012.

Gophotonics, "NL200 series," Data Sheet, pp. 1-3, Jun. 29, 2017.

Rashad, "What is the Easiest Way to do YAG Laser Posterior Capsulotomy?", YouTube Clip, p. 1, Jul. 17, 2020 https://www.youtube.com/watch?v=g0pV3UGo_20.

"Smart Selecta Duet—Your Smart Selection for Glaucoma Care," Product Brochure, pp. 1-6, The Lumenis Group of Companies, year 2018.

Rashad, "How to do Yag Laser Posterior Capsulotomy in Small Pupil?", YouTube Clip, p. 1, Jul. 19, 2020 https://www.youtube.com/watch?v=12c39BoNBjM.

Quantel Medical, "Optimis II", datasheet, pp. 1-4, Aug. 5, 2022.

Variscite, "DART-MX8M", Datasheet, pp. 1-92, Feb. 2021.

Sridhar, "Anatomy of Cornea and Ocular Surface," Indidan Journal of Ophthalmology, vol. 66, issue 2, pp. 190-194, year 2018.

JP Application # 2022567443 Office Action dated Dec. 17, 2024.

Extended European Search Report for application No. 24203656.4, dated Jun. 5, 2025.

Nagar et al., "A randomised, prospective study comparing selective laser trabeculoplasty with latanoprost for the control of intraocular pressure in ocular hypertension and open angle glaucoma," British Journal of Ophthalmology, vol. 89, pp. 1413-1417, year 2005.

Hong et al., "Repeat Selective Laser Trabeculoplasty," Journal of Glaucoma, vol. 18, issue 3, pp. 180-183, Mar. 2009.

Goyal et al., "Effect of primary selective laser trabeculoplasty on tonographic outflow facility—a randomised clinical trial," British Journal of Ophthalmology, BMJ Publishing Group, vol. 94, issue 11, pp. 1-22, year 2010.

Franco et al., "Effect of Second SLT on IOP," Investigative Ophthalmology & Visual Science, vol. 48, pp. 1-2, May 2007.

Chen et al., "A Comparison between 90 degrees and 180 degrees Selective Laser Trabeculoplasty," Journal of Glaucoma, vol. 13, issue 1, p. 1, Feb. 2004.

Mequio et al, "Efficacy of Repeat Selective Laser Trabeculoplasty," Investigative Ophthalmology & Visual Science, vol. 48, p. 1, year 2007.

Grulkowski et al., "Anterior segment imaging with Spectral OCT system using a high-speed CMOS camera," Optics Express, vol. 17, No. 6, p. 4842-4858, year 2009.

Shields et al., "Noncontact Transscleral ND:YAG Cyclophotocoagulation: A Long-Term Follow-Up of 500 Patients," Transactions of the American Ophthalmological Society, vol. XCII, pp. 271-287, year 1994.

Liu et al., "Real-time visual analysis of microvascular blood flow for critical care," CVPR2015 paper as Open Access Version, provided by the Computer Vision Foundation, pp. 2217-2225, year 2015.

Desco et al., "Effect of prophylactic brimonidine on bleeding complications after cataract surgery," European Journal of Ophthalmology, vol. 15, pp. 228-232, year 2005.

Pasquali et al., "Dilute brimonidine to improve patient comfort and subconjunctival hemorrhage after LASIK," Journal of Refractive Surgery, vol. 29, pp. 469-475, year 2013.

Sacks et al., "Non-contact direct selective laser trabeculoplasty: light propagation analysis," Biomedical Optics Express, vol. 11, pp. 2889-2904, year 2020.

Kasuga et al., "Trabecular Meshwork Length in Men and Women by Histological Assessment," Current Eye Research, Early Online, pp. 1-5, Jun. 2012.

Navilas Operator Manual, Document Version 2.10, 2012 OD-OS GmbH, pp. 1-94, Sep. 2012.

SensoMotoric Instruments GmbH (SMI), "SG 3000", Product Flyer, pp. 1-2, year 2010.

Ashik et al., "The precision of ophthalmic biometry using calipers," Canadian Journal of Ophthalmology, vol. 48, issue 6, pp. 1-13, Dec. 2013.

Balalzsi, "Noncontact Thermal Mode Nd:YAG Laser Transscleral Cyclocoagulation in the Treatment of Glaucoma," Ophthalmology, vol. 98, pp. 1858-1863, year 1991.

Leung et al., "Anterior chamber angle imaging with optical coherence tomography," Eye, vol. 25, pp. 261-267, year 2011.

Tasman et al., "The Wills Eye Hospital Atlas of Clinical Ophthalmology," Lippincott Williams & Wilkins, p. 158, year 2001.

Gaasterland, "Laser Therapies: Iridotomy, Iridoplasty, and Trabeculoplasty," as appears in "The Glaucoma Book: A Practical Evidence-Based Approach to Patient Care," Springer, p. 722, year 2010.

Kara, "Bleeding in Retinal Images Using image Processing", A Thesis submitted to the graduate school of applied sciences of Near East University, Nicosia, Larnaca, pp. 1-79, year 2019.

Chinese Office Action #202180071581.6 dated Apr. 25, 2025.

(56)                References Cited

OTHER PUBLICATIONS

Australian Examination 1st Report, #2024205587 dated Jul. 10, 2025.
EP Communication pursuant to rules 70 (2) and 70a (2) EPC #25152129.0.
Extended European Search Report #25152129.0 dated Apr. 3, 2025.
JP Notice of Allowance # 2023-217477 dated May 7, 2025.
JP Office Action #2023-519588 dated Aug. 5, 2025
JP Office Action #2022-567443 dated May 7, 2025.
Singapore Written Opinion #11202200506U dated Apr. 17, 2025.
U.S. Appl. No. 17/427,926 Office Action dated May 9, 2024.
EP Application # 19877990.2 Office Oction dated May 13, 2024.
EP Application # 24158977.9 Search Report dated May 15, 2024.
EP Applicatian # 21845437.9 Search Report dated Jun. 19, 2024.
JP Application # 2023217477 Office Action dated Jul. 9, 2024.
U.S. Appl. No. 17/273,323 Office Action dated Jun. 18, 2024.
International Application # PCT/IB2023/061472 Search Report dated Feb. 29, 2024.
Kohnen et al., "Internal Anterior Chamber Diameter using Optical Coherence Tomography Compared with White-To-White Distances using Automated Measurements," Journal of Cataract & Refractive Surgery, vol. 32, pp. 1809-1813, Nov. 2006.
Zhang et al., "Perioperative Medications for Preventing Temporarily Increased Intraocular Pressure after Laser Trabeculoplasty (Review)," Cochrane Database of Systematic Reviews 2017, issue 2, pp. 1-117, year 2017.
Katta et al., "Optical Coherence Tomography Image-Guided Smart Laser Knife for Surgery," Lasers in Surgery and Medicine, Wiley Online Library, pp. 1-11, Jul. 2017.
Barnes et al., "Control of Intraocular Pressure Elevations after Argon Laser Trabeculoplasty: Comparison of Brimonidine 0.2% to Apraclonidine 1.0%," Opthalmology, vol. 106, No. 10, pp. 2033-2037, year 1999.
Yakopson et al., "Brimonidine 0.1% vs. Apraclonidine 0.5% for Prevention of Intraocular Pressure Elevation after Selective Laser Trabeculoplasty," Investigative Ophthalmology & Visual Science, vol. 49, p. 1234, May 2008.
Kim et al., "Effect of Prophylactic Topical Brimonidine (0.15%) Administration on the Development of Subconjunctival Hemorrhage after Intravitreal Injection," Retina, The Journal for Retinal and Vitreous Diseases, vol. 31, No. 2, pp. 389-392, year 2011.
Hong et al., "Effect of Prophylactic Brimonidine Instillation on Bleeding during Strabismus Surgery in Adults," American Journal of Ophthalmology, vol. 144, No. 3, pp. 469-470, Sep. 2007.
Goldsmith et al., "Anterior Chamber Width Measurement by High-Speed Optical Coherence Tomography," Ophthalmology, vol. 112, No. 2, pp. 238-244, year 2005.
Norden, "Effect of Prophilactic Brimonidine on Bleeding Complications and Flap Adherence After Laser in situ Keratomileusis," Journal of Refractive Surgery, vol. 18, No. 4, pp. 468-471, Jul./Aug. 2002.
EP Application # 21885460.2 Search Report dated Aug. 26, 2024.
EP Application # 19830473.5 Office Action dated Sep. 3, 2024.
U.S. Appl. No. 17/273,323 Office Action dated Oct. 30, 2024.
U.S. Appl. No. 17/427,926 Office Action dated Aug. 27, 2024.

* cited by examiner

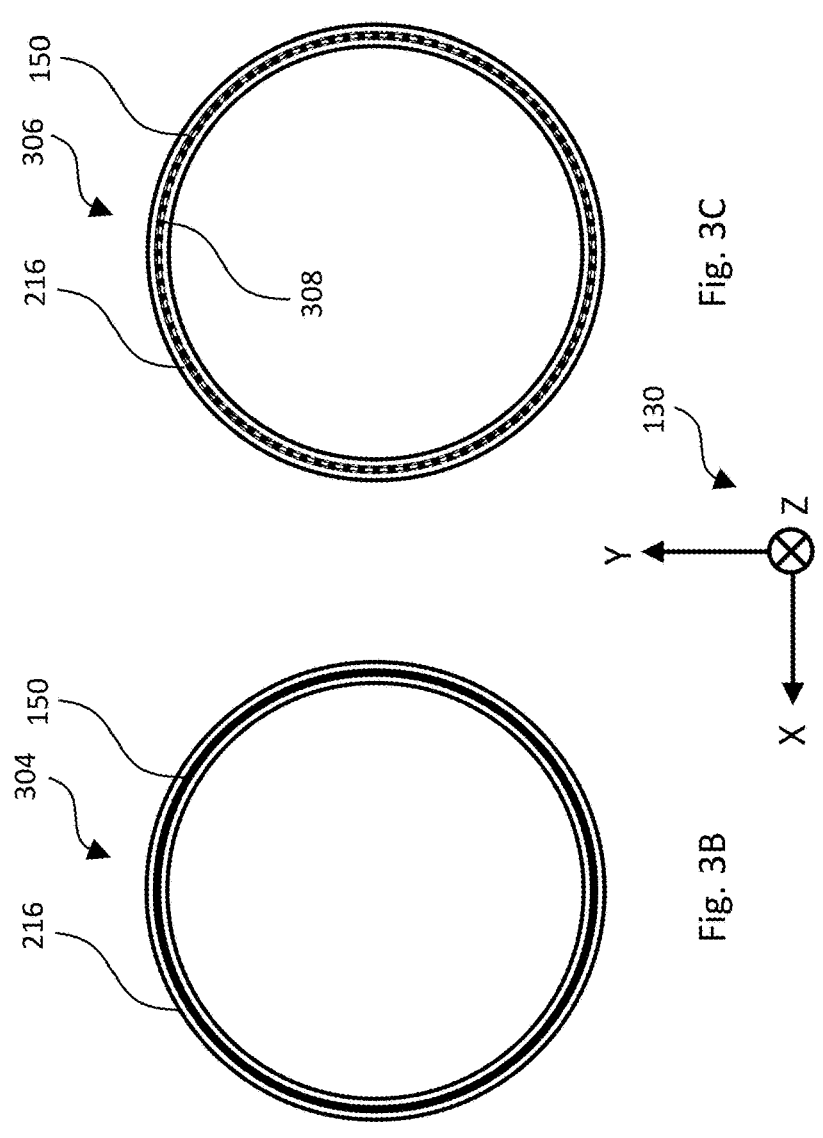
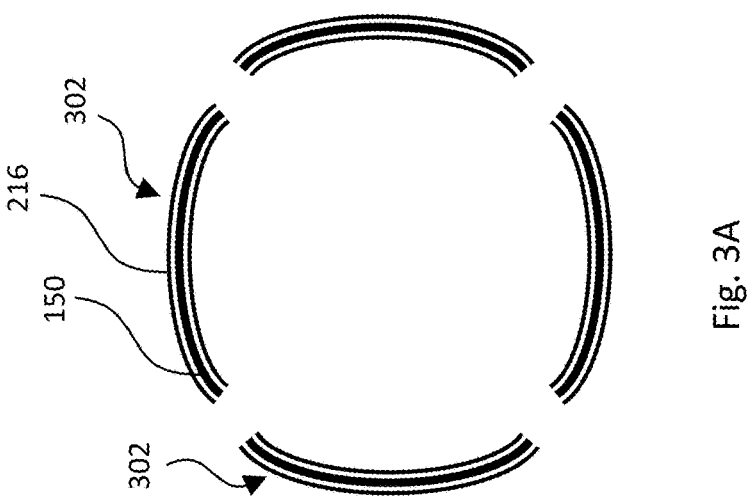
Fig. 3C
Fig. 3B
Fig. 3A

500

502 — start

504 — position head in proximity to gonioscope

506 — align optical unit in XY to the eye

508 — move optical unit in Z to contact the eye

510 — center and focus eye to gonioscope

512 — capture image of the eye through gonioscope

514 — process image to generate locus of laser targets

516 — verify locus of laser targets

518 — fire laser to targets

520 — end

GONIOSCOPIC LASER SURGERY

CROSS-REFERENCE TO RELATED APPLICATION

This application is a continuation in part of PCT Patent Application PCT/IB2023/060104, filed Oct. 9, 2023, which claims the benefit of U.S. Provisional Patent Application 63/414,919, filed Oct. 11, 2022. Both of these related applications are incorporated herein by reference.

FIELD OF THE INVENTION

The present invention relates generally to apparatuses and methods for treatment of the eye, and particularly to laser trabeculoplasty.

BACKGROUND

Glaucoma is a group of eye diseases that lead to damage of the optic nerve. This damage is often caused by increased intraocular pressure (TOP) of the aqueous humor within the anterior chamber of the eye. This increased IOP may cause vision loss if left untreated.

One of the treatments used to reduce IOP is selective laser trabeculoplasty (SLT), which is described, for example, by Gazzard et al. in "*Selective laser trabeculoplasty versus drops for newly diagnosed ocular hypertension and glaucoma: the LiGHT RCT*" (NHS, volume 23, issue 31, June 2019, ISSN 1366-5278). In SLT, several laser shots are fired through the anterior chamber to the trabecular meshwork of the eye using a gonioscope. The laser irradiation of the trabecular meshwork improves the drainage of aqueous humor through the meshwork, thus alleviating the build-up of IOP within the eye.

The term "optical radiation" is used in the present description and in the claims to refer to electromagnetic radiation in any of the visible, infrared, and ultraviolet ranges of the spectrum.

SUMMARY

Embodiments of the present invention that are described hereinbelow provide improved apparatuses and procedures for selective laser trabeculoplasty.

There is therefore provided, in accordance with an embodiment of the invention, an apparatus for medical treatment. The apparatus includes a gonioscope having a distal face, which is configured for placement in proximity to an eye of a patient, a proximal face opposite the distal face, and multiple facets extending between the distal and proximal faces; a camera that is configured to capture, through the proximal face of the gonioscope, an image of an anterior chamber of the eye; and a laser configured to generate a beam of optical radiation. The apparatus further includes a scanner, which is configured to direct the beam through the proximal face of the gonioscope so that the beam reflects from a facet of the gonioscope into the anterior chamber to impinge on tissue in the anterior chamber, and optics configured to focus the beam to impinge on the tissue in the anterior chamber with a cone angle no greater than 2°. A controller is configured to process the image of the anterior chamber so as to identify a locus of a trabecular meshwork in the eye and to control the scanner so as to direct the beam to impinge on the identified locus at multiple locations around a circumference of the anterior chamber.

In a disclosed embodiment, the optics are configured to focus the beam so that the cone angle is less than 1.5°.

In a further embodiment, the camera has a depth of field sufficient to image all of the circumference of the anterior chamber through the gonioscope at a fixed focal setting. Typically, the optics are configured to direct the beam to impinge on all the multiple locations around the circumference of the anterior chamber at the fixed focal setting. Alternatively of additionally, the depth of field of the camera is at least 4 mm. Further alternatively, the depth of field is at least 3 mm, 2 mm, or 1 mm.

In yet another embodiment, in the image captured by the camera, the circumference of the anterior chamber is divided into multiple segments due to reflection of parts of the image from the multiple facets of the gonioscope, and the processor is configured to stitch together the multiple segments to generate an output image in which the locus of the trabecular meshwork appears as a continuous band.

In a disclosed embodiment, the distal face of the gonioscope includes a concave surface configured to contact a cornea of the eye. The apparatus may include a suction ring surrounding the gonioscope and configured to maintain a stable contact between the eye and the gonioscope.

There is also provided, in accordance with an embodiment of the invention, a method for medical treatment. The method includes positioning a distal face of a gonioscope in proximity to an eye of a patient, capturing through the gonioscope an image of an anterior chamber of the eye, processing the image of the anterior chamber so as to identify a locus of a trabecular meshwork in the eye and directing a beam of optical radiation emitted by a laser through the proximal face of the gonioscope so that the beam reflects from a facet of the gonioscope into the anterior chamber and impinges on the identified locus in the anterior chamber at multiple locations around a circumference of the anterior chamber, while focusing the beam to impinge on the tissue in the anterior chamber with a cone angle no greater than 2°.

There is additionally provided, in accordance with an embodiment of the invention, a method for medical treatment, which includes positioning a distal face of a gonioscope in proximity to an eye of a patient and capturing, through the gonioscope, an image of an anterior chamber of the eye. The image of the anterior chamber is processed so as to identify a locus of a trabecular meshwork in the eye. A beam of optical radiation emitted by a laser is directed through the proximal face of the gonioscope so that the beam reflects from a facet of the gonioscope into the anterior chamber and impinges on the identified locus in the anterior chamber at multiple locations around a circumference of the anterior chamber using a fixed focal setting of the beam at all the multiple locations around the circumference of the anterior chamber.

In a disclosed embodiment, capturing the image of the anterior chamber comprises capturing the image with a depth of field sufficient to image all of the circumference of the anterior chamber through the gonioscope at the fixed focal setting.

There is additionally provided, in accordance with an embodiment of the invention, an apparatus for medical treatment. The apparatus includes a gonioscope having a distal face, which is configured for placement in proximity to an eye of a patient, a proximal face opposite the distal face, and multiple facets extending between the distal and proximal faces. The apparatus further includes a laser configured to generate a beam of optical radiation, and a scanner, which is configured to direct the beam through the proximal face of the gonioscope so that the beam reflects from a facet of the gonioscope into an anterior chamber of the eye. At least one slit lamp is configured to project at least one sheet of light into the eye through the gonioscope, and a camera is configured to capture, through the gonioscope, an image of an illumination pattern cast on the eye by the at least one sheet of light. The apparatus also includes a processor, which is configured to process the image of the illumination pattern so as to identify a location of an anatomical structure in the eye, to select one or more targets in the eye based on the identified location, and to control the scanner so that the beam impinges on the one or more targets.

In a disclosed embodiment, the processor is configured to identify the location of a trabecular meshwork in the eye based on the image of the illumination pattern.

In a further embodiment, the processor is configured to select one or more targets so that the beam irradiates the trabecular meshwork in the eye.

In another embodiment, the at least one slit lamp is configured to project the at least one sheet of light onto a cornea and an iris of the eye, and the processor is configured to process the image of the illumination pattern so as to identify an angle of an anterior chamber of the eye.

In yet another embodiment, the processor is configured to identify the angle of the anterior chamber by finding a bend in the illumination pattern.

In a further embodiment, the apparatus includes an optical coherence tomography (OCT) unit coupled to the processor and configured to map a three-dimensional (3D) structure of the eye, and the processor is configured to select the one or target points responsively to the 3D structure.

In another embodiment the at least one slit lamp is configured to project multiple sheets of light into the eye through respective facets of the gonioscope.

There is further provided, in accordance with an embodiment of the invention, an apparatus for medical treatment. The apparatus includes a gonioscope having a distal face, which is configured for placement in proximity to an eye of a patient, and a proximal face opposite the distal face, an optical unit movable axially and transversely relative to an optical axis of the eye, and a fixture for coupling the gonioscope to the optical unit while aligning the optical unit with the eye through the gonioscope. The fixture includes a mechanical stage configured to move transversely to the optical axis of the eye so as to follow transverse movement of the optical unit, a first part attached to the optical unit, and a second part attached to the gonioscope and configured to move axially relative to the first part. A first lock is configured to lock and unlock the second part to the first part, and a second lock is configured to lock and unlock the second part to the mechanical stage.

In a disclosed embodiment, the first and second parts include concentric cylinders of different, respective diameters.

In a further embodiment, the first lock fixes a depth of insertion of one of the concentric cylinders within the other of the concentric cylinders.

In another embodiment, the second lock fixes an axial location of the second part of the fixture relative to the eye of the patient.

In yet another embodiment, the first and second locks include respective pins that are inserted into and retracted from respective holes.

In a disclosed embodiment, the alignment of the optical unit with the eye includes an axial alignment step with the first lock closed and the second lock open, followed by a transverse alignment step with the first lock open and the second lock closed.

In a further embodiment, the optical unit includes a camera configured to capture an image of the eye through the proximal face of the gonioscope.

In another embodiment, the optical unit includes a laser configured to irradiate the eye with a beam of radiation directed through the gonioscope.

In yet another embodiment, the optical unit includes a scanner, which is configured to direct the beam through the proximal face of the gonioscope so that the beam reflects from a facet of the gonioscope into an anterior chamber of the eye to impinge on tissue in the anterior chamber.

In a further embodiment, the apparatus includes a chin rest, to which the mechanical stage is attached so as to allow shifting the fixture transversely relative to the eye in conjunction with the optical unit while a chin of the patient rests on the chin rest.

There is additionally provided, in accordance with an embodiment of the invention, a method for medical treatment. The method includes positioning a distal face of a gonioscope in proximity to an eye of a patient, and projecting at least one sheet of light into the eye through the gonioscope, capturing through the gonioscope an image of an illumination pattern cast on the eye by the at least one sheet of light. The method further includes processing the image of the illumination pattern so as to identify a location of an anatomical structure in the eye, selecting one or more targets in the eye based on the identified location, and directing a beam of optical radiation emitted by a laser through a proximal face of the gonioscope so that the beam impinges on the one or more targets.

There is further provided, in accordance with an embodiment of the invention, a method for medical treatment. The method includes positioning a distal face of a gonioscope in proximity to an eye of a patient, and coupling the gonioscope to an optical unit, which is movable axially and transversely relative to an optical axis of the eye, using a fixture. The fixture includes a mechanical stage configured to move transversely to the optical axis of the eye so as to follow transverse movement of the optical unit. The fixture further includes a first part attached to the optical unit, a second part attached to the gonioscope and configured to move axially relative to the first part, a first lock configured to lock and unlock the second part to the first part, and a second lock configured to lock and unlock the second part to the mechanical stage. The method further includes aligning the optical unit with the eye through the gonioscope using the fixture.

The present invention will be more fully understood from the following detailed description of the embodiments thereof, taken together with the drawings in which:

BRIEF DESCRIPTION OF THE DRAWINGS

FIGS. 3A, 3B and 3C are schematic representations of segments of an anterior chamber angle in three successive stages of processing of a gonioscopic image, in accordance with an embodiment of the invention;

DETAILED DESCRIPTION OF EMBODIMENTS

Overview

Figure 1:
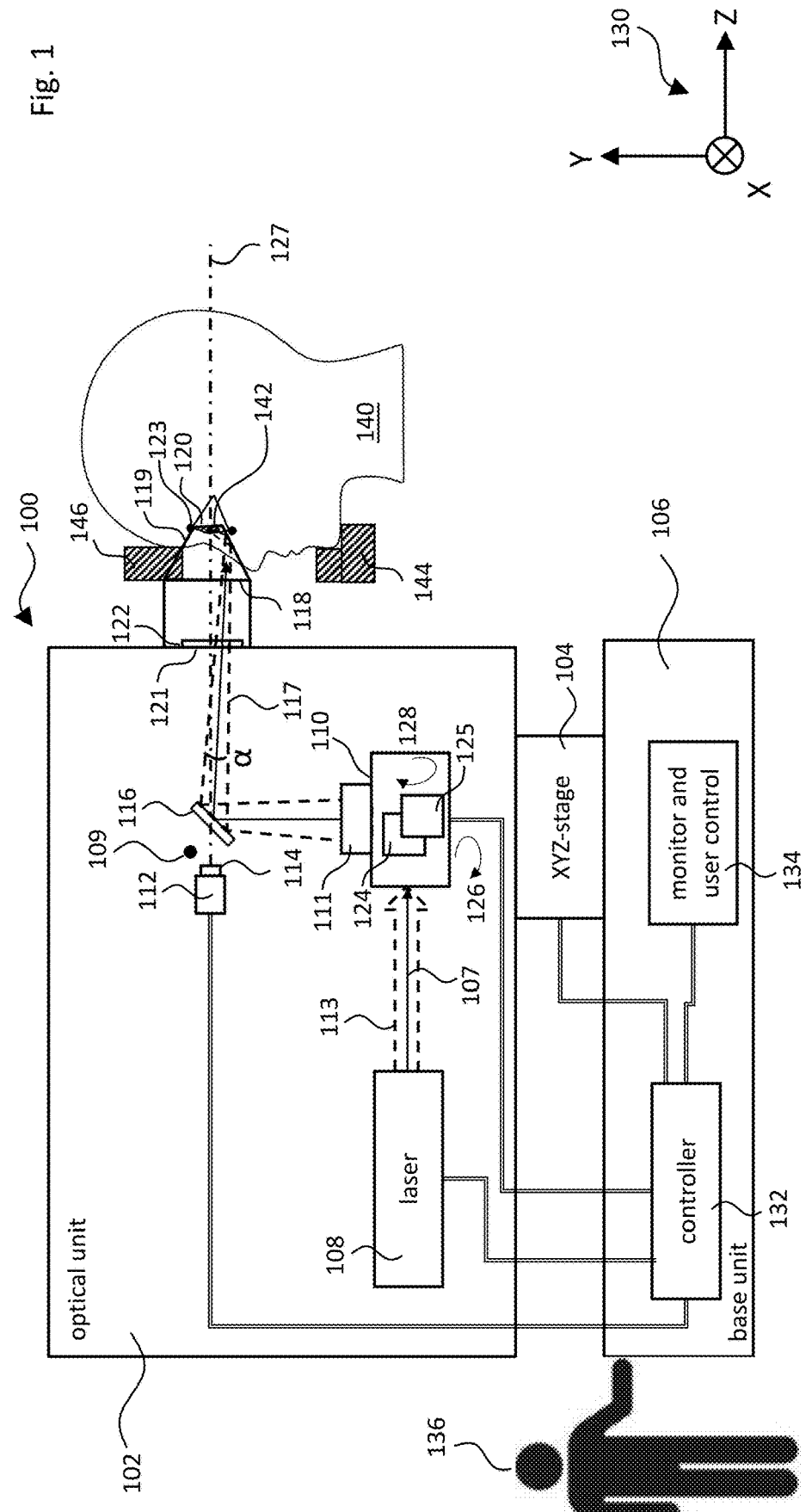
FIG. 1 is a schematic side view of an SLT apparatus, in accordance with an embodiment of the invention.

In an SLT procedure, a patient is seated in front of the SLT apparatus, which is aligned to the patient's eye. The patient must remain with his/her head in a fixed position and orientation with respect to the SLT apparatus while the laser beam is focused on and shifted across the trabecular meshwork by the operating ophthalmologist. As in other laser surgical procedures, the laser beam is focused precisely onto each point in the trabecular meshwork that is to be treated as indicated by the sharp focus of an aiming beam through a surgical microscope. (The proper location of the treatment beam corresponds with the focus of the surgical microscope.) Because of irregularities in the eye and in positioning of the gonioscope, the focal position often varies from point to point. Furthermore, to ensure that the laser beam is properly aimed and focused, it is necessary to refocus the microscope that the ophthalmologist uses to view the gonioscopic images. As a large number of laser pulses are fired into the trabecular meshwork with concomitant alignment and focusing of the surgical microscope and the laser beam, the procedure may be prolonged, taxing the stamina of the ophthalmologist performing the procedure, as well as the ability of the patient to keep his/her head in a fixed position and orientation.

There is thus a need to automate and shorten the duration of the SLT procedure while ensuring that its efficacy is maintained. Some embodiments of the present invention that are described herein address this problem by employing a laser emitting a beam that is only loosely focused, with a small cone angle, for example less than 2°. This innovation is based on the realization that the effectiveness of laser trabeculectomy is not dependent on creating a precise intensity on the trabecular meshwork. The use of a loosely focused beam in the present embodiments provides a large depth of field for the laser beam, thus relaxing the requirements for focusing the beam and speeding up the procedure. Under these conditions, the same focal setting can be generally used around the entire circumference of the anterior chamber. This arrangement also makes it possible to use a camera with a large depth of field for aligning the laser beam.

Some embodiments of the present invention provide an apparatus for medical treatment, comprising a gonioscope having a distal face, which is configured for placement in proximity to an eye of a patient, a proximal face opposite the distal face, and multiple facets extending between the distal and proximal faces. A camera captures, through the proximal face of the gonioscope, an image of the anterior chamber of the eye. A laser generates a beam of optical radiation, and a scanner directs the beam through the proximal face of the gonioscope so that the beam reflects from a facet of the gonioscope into the anterior chamber to impinge on tissue in the anterior chamber. In some embodiment, optics focus the beam to impinge on the tissue in the anterior chamber with a cone angle no greater than 2°, and possibly less than 1.5°. Alternatively, larger cone angles may be used. A controller processes the image of the anterior chamber so as to identify the locus of the trabecular meshwork in the eye and to control the scanner so as to direct the beam to impinge on the identified locus at multiple locations around a circumference of the anterior chamber.

In another embodiment, a slit lamp source is integrated into the SLT apparatus. The slit lamp projects a thin sheet of light through one or more facets of the gonioscope onto the area of the cornea and iris. The shape of the pattern of light reflected from the cornea and iris assists in identifying landmarks in the eye around the trabecular meshwork. These landmarks, in turn, assist in identifying the targets for the focused laser beam.

A further embodiment provides a novel fixture, referred to herein as a "goniocone," for simplifying alignment of the apparatus during the SLT procedure. In a typical SLT procedure (without the goniocone), the attention of the operator is required for two alignment tasks: The operator adjusts the position of the optical unit of the apparatus with one hand (e.g., with a joystick) and, at the same time, uses the other hand to hold and align the gonioscope to the patient's eye. The goniocone simplifies these tasks by holding the gonioscope in position against the eye, thus relieving the operator of the need to hold the gonioscope during the procedure.

In a disclosed embodiment, the goniocone comprises two parts, for example concentric cylinders, with the first part attached to the optical unit and the second part attached to the gonioscope. In an initial alignment step, the two parts of the goniocone are locked together, so that the gonioscope moves rigidly with the optical unit. During the subsequent stages of the procedure, the second part of the goniocone is unlocked from the first part and locked into a mechanical stage, which follows the movement of the optical unit only in the transverse directions with respect to the optical axis of the eye. The mechanical stage is coupled to the same mechanical reference as the patient (e.g., a chin rest). Thus, during these subsequent stages, the operator is free to adjust the position of the optical unit both in the transverse directions and in the direction of the optical axis of the eye (focusing) without the risk of an inadvertent movement of the gonioscope in the direction of the patient's eye.

SYSTEM DESCRIPTION

FIG. 1 is a schematic side view of a partially automated SLT apparatus 100, in accordance with an embodiment of the invention.

SLT apparatus 100 comprises an optical unit 102, an XYZ-stage 104, and a base unit 106. Optical unit 102 comprises a treatment laser 108 emitting a treatment beam 113 of optical radiation and an optional low-intensity integrated collinear aiming beam 107, which may include its separate focusing optics (not shown). The optical unit also comprises a scanner 110, a camera 112, a camera lens 114, a fixation point 109, and a beam combiner 116, which combines the optical paths of laser 108 and camera 112. Focusing optics 111 focus treatment beam 113 emitted by laser 108 and scanned by scanner 110 into a focused treatment beam 117 with a cone angle α no greater than 2°. In an alternative embodiment, cone angle α may be limited by optics 111 to no greater than 1.5°. For focusing beam 113, optics 111 may, in an alternative embodiment, be positioned between laser 108 and scanner 110. Optics 111 may also comprise a focusing mechanism.

In the present example, laser 108 comprises a frequency-doubled Nd:YAG Q-switched laser, emitting pulses at a wavelength of 532 nm with a pulse duration in the range of 1-10 nanoseconds, pulse frequency 1-100 Hz, and pulse energy ranging from 0.2 mJ to 2.6 mJ. Alternatively, any other suitable type of laser may be used, operating in either pulsed or CW mode.

Optical unit 102 further comprises a gonioscope 118, comprising multiple reflecting facets 119 arranged in a truncated cone between a distal face 120 and a proximal face 121, and an illumination ring 122. In the examples shown in the figures that follow, the gonioscope has four or six facets; but alternatively, the gonioscope may comprise any suitable number of facets or may have a continuous curved shape. Distal face 120 is concave and in certain embodiments is surrounded by a suction ring 123 to maintain a stable contact between the patient's eye and the gonioscope. Gonioscope 118 is collinear with and centered on an optical axis 127 of camera 112.

In the pictured embodiment, scanner 110 comprises two galvanometer mirrors 124 and 125 rotating around two orthogonal axes (not shown for the sake of simplicity), with the rotations indicated by respective circular arrows 126 and 128. Scanner 110 is configured to direct beam 117 through proximal face 121 of gonioscope 118 so that the beam reflects from a facet 119 of the gonioscope through distal face 120 into an anterior chamber 129 (FIG. 4A) of an eye 142 in contact with the distal face so as to impinge on tissue in the anterior chamber. Alternatively, other types of scanners may be used. For example, scanner 110 may comprise voice-coil activated mirrors.

XYZ-stage 104 moves optical unit 102 in the three linear orthogonal X-, Y-, and Z-directions, as indicated by Cartesian coordinates 130. In this and subsequent figures, the Z-direction corresponds to optical axis 127.

Base unit 106 comprises a controller 132, as well as a monitor and user control unit 134. Controller 132 is coupled to camera 112, laser 108, scanner 110, XYZ-stage 104, and monitor and user control unit 134. Alternatively, the monitor and/or the entire user control unit 134 and/or the controller may be integrated in the optical unit 102.

Controller 132 typically comprises a programmable processor, which is programmed in software and/or firmware to carry out the functions that are described herein. Alternatively or additionally, controller 132 comprises hard-wired and/or programmable hardware logic circuits, which carry out at least some of the functions of the controller. Although controller 132 is shown in the figure, for the sake of simplicity, as a single, monolithic functional block, in practice the controller may comprise a single chip or a set of two or more chips, with suitable interfaces for receiving and outputting the signals that are illustrated in the figure and are described in the text.

Monitor and user control unit 134 comprises one or more visual displays and suitable input devices, such as a keyboard, joystick, and/or mouse, enabling an operator 136 to interact with SLT apparatus 100. (Details of monitor and user control unit 134 have been omitted from the figure for the sake of simplicity.)

For an SLT procedure, a patient positions his/her head 140 in front of optical unit 102, so that his/her eye 142 is in proximity to distal face 120 of gonioscope 118. Apparatus 100 typically comprises a chin rest 144 and a forehead rest 146 for enhanced stability of patient's head 140 during the procedure. Chin rest 144 and forehead rest 146 may be integrated into base unit 106 or attached to a table of apparatus 100. Fixation point 109 is provided for the patient to align and stabilize his/her eye 142.

Figure 4A:
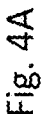
FIGS. 4A and 4B are sectional and frontal partial views of the eye, respectively, showing a beam of a laser of the SLT apparatus and indicating a depth of field of the camera, in accordance with an embodiment of the invention.
Figure 4A:
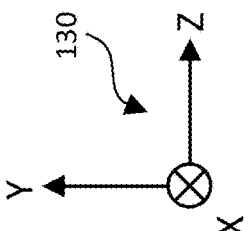

Operator 136 observes eye 142 in an image captured by camera 112 and displayed on a monitor of unit 134. For this purpose, eye 142 may be illuminated by illumination ring 122, for example, although alternatively, other sorts of light sources may be used. Camera 112, together with lens 114, has a depth of field sufficient to image the entire circumference of anterior chamber 129 of eye 142 at a single focal setting of the camera. While observing the eye, operator 136 moves, with an input device such as a joystick, optical unit 102 in the X- and Y-directions so that optical axis 127 of camera 112 is aligned with eye 142. Operator 136 then moves optical unit 102 in the Z-direction to bring the concave surface of distal face 120 into contact with the cornea of eye 142 (FIG. 4A). Prior to making contact, a gel or other suitable contact material may be applied to cornea 149. In certain embodiments suction ring 123 maintains a stable contact between eye 142 and gonioscope 118.

Figure 2:
FIG. 2 is a schematic representation of a frontal image of an anterior chamber of an eye captured by a camera through a gonioscope, in accordance with an embodiment of the invention.
Figure 2:
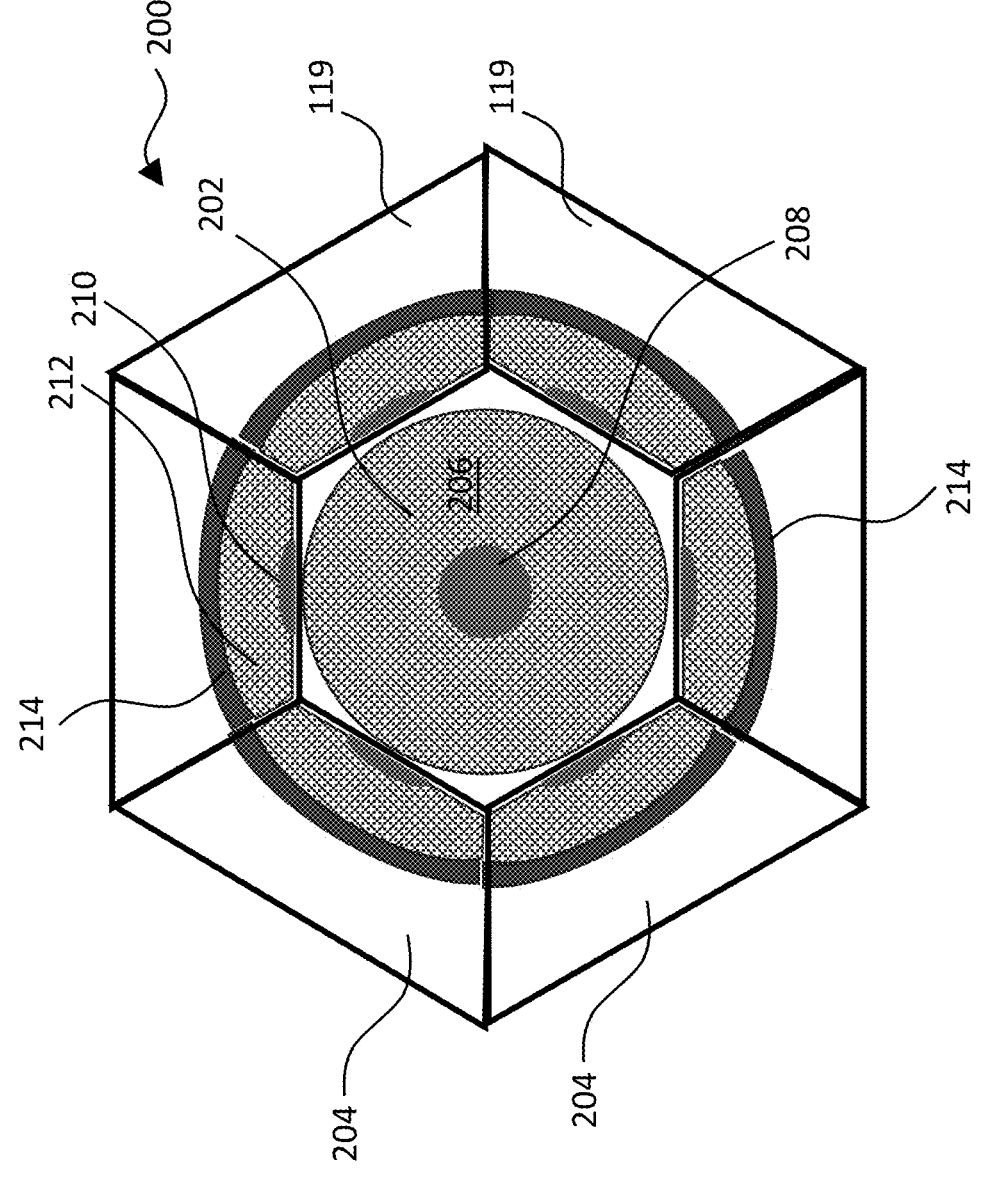

After the alignment process described hereinabove, operator 136 fine-tunes the XY-position of optical unit 102 so as to center eye 142 in the field of view of camera 112 and image an entire 360° field of view (for example as shown in FIG. 2). The same fixed focal setting is used around the entire circumference of anterior chamber 129, and there is no need to refocus camera 112 at different points around the circumference, even if the image is not perfectly sharp at all points. As will be further detailed with reference to FIGS. 3A-3C hereinbelow, controller 132 identifies the locus of the trabecular meshwork of eye 142 in an image captured by camera 112, and then directs scanner 110 to direct beam 117 to impinge on the trabecular meshwork at multiple locations around the circumference of the anterior chamber during the procedure. Before the actual firing of laser 108, operator 136 verifies the position of locus 308 on the trabecular meshwork and the alignment of the laser using aiming beam 107 displayed on the monitor. Once laser 108 is activated to emit beam 113, a typical procedure may take less than a minute and possible only a few seconds using a pulse frequency of 50-100 Hz and pulse energy of ~1 mJ. Prior to emitting treatment beam 113, aiming beam 107 may be swept over the target points with operation verified by operator 136 before proceeding to treatment mode.

FIG. 2 is a schematic representation of a frontal image 200 of the anterior chamber of eye 142 captured by camera 112 through gonioscope 118, in accordance with an embodiment of the invention.

Image 200 comprises both a direct image 202 of the anterior chamber and reflected images 204 reflected by facets 119 of gonioscope 118. In the embodiment shown in FIG. 2, gonioscope 118 comprises six reflecting facets 119; in alternative embodiments the number of facets 119 may be less or more than six, such as four, eight, twelve, or any other number of facets.

Direct image 202 comprises an image of an iris 206 and a pupil 208 of eye 142, without reflections from facets 119. Each reflected image 204 may comprise a partial iris image 212 and may comprise a partial pupil image 210. Furthermore, each reflected image 204 comprises an image segment 214 of the angle of the anterior chamber (as shown in FIG. 4A), which corresponds to the locus of a respective part of the trabecular meshwork. Due to the large depth of field of camera 112, image segments 214, reflected by respective facets 119, may be brought simultaneously into sufficient focus on the camera in all reflected images 204 to aim the weakly focused treatment beam 117, avoiding the need to re-focus the camera onto different parts of the anterior chamber angle and thus speeding up the procedure. Due to the optical construction of gonioscope 118, however, image segments 214 are distorted and separated from each other, as will be further detailed with reference to FIG. 3A, hereinbelow.

FIGS. 3A-3C schematically show image segments 302 of an angle 216 of the anterior chamber over a 360° circumference in three respective stages of processing of an image captured by camera 112, in accordance with an embodiment of the invention.

FIG. 3A shows image segments 302 of anterior chamber angle 216 captured through a gonioscope (similar to gonioscope 118 but with four reflecting facets). A trabecular meshwork 150 of the eye is located within angle 216. As indicated in FIG. 2 hereinabove, image segments 302, as captured by camera 112, are distorted from their actual shape, as well as separated from each other.

FIG. 3B is a schematic image 304 of an (in general) elliptical and continuous image of anterior chamber angle 216 and trabecular meshwork 150, wherein controller 132 has un-distorted and stitched image segments 302 in order to identify a locus of the trabecular meshwork.

FIG. 3C is a schematic image 306, in which controller 132 has identified a locus 308 (dotted line) of trabecular meshwork 150, along a circumference of the anterior chamber.

Controller 132 will control laser 108 and scanner 110 to fire and direct laser beam 117 to impinge on the trabecular meshwork at multiple locations around locus 308.

Figure 4B:
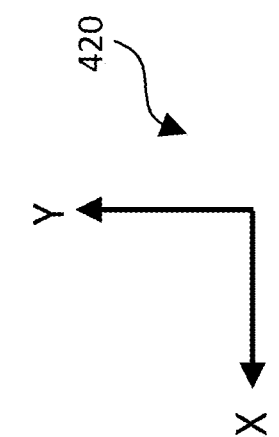
Figure 4B:
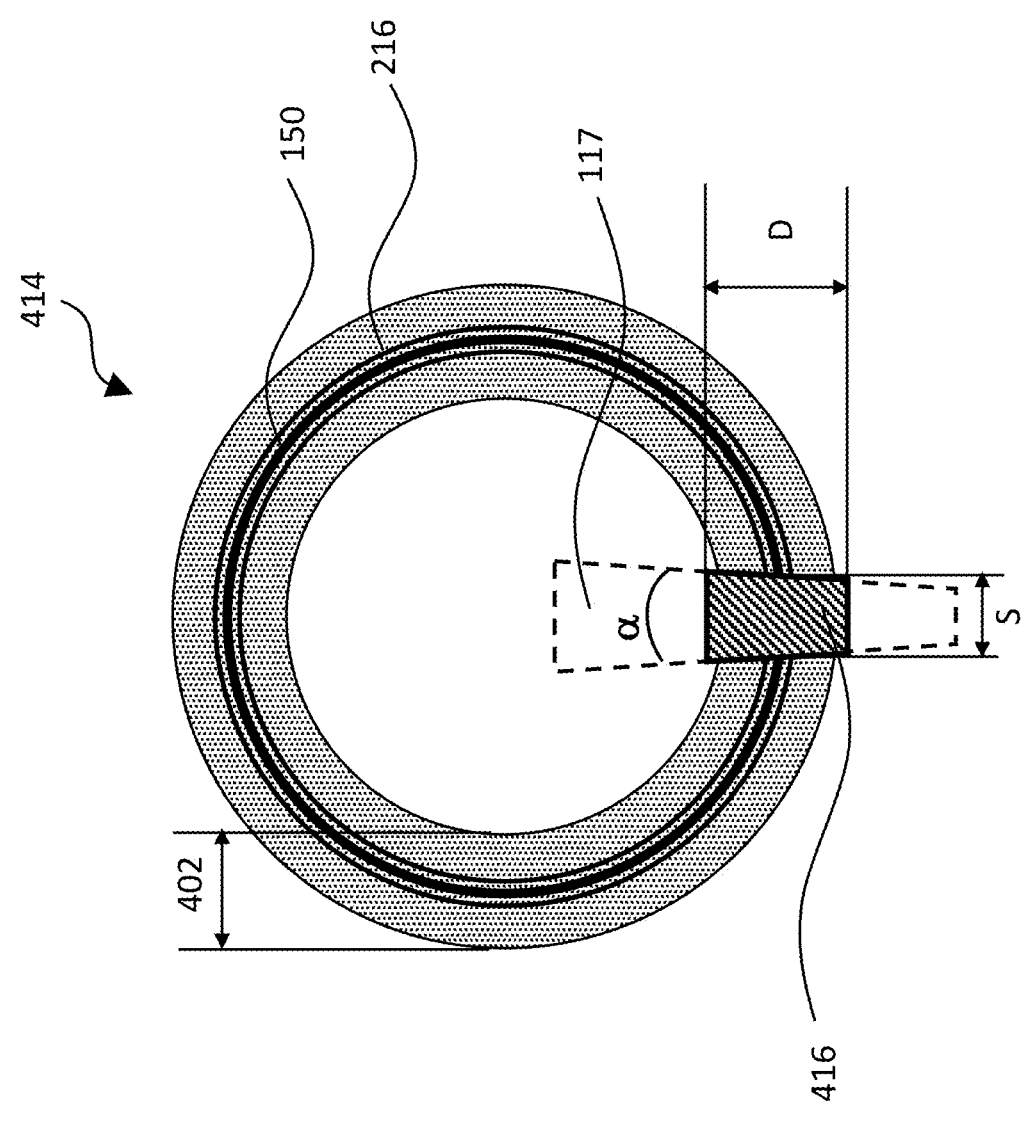

FIGS. 4A and 4B schematically show a sectional partial view 404 and a frontal partial view 414 of eye 142, showing beam 117 of laser 108 and indicating a depth of field 402 of camera 112, in accordance with an embodiment of the invention.

Sectional view 404 in FIG. 4A comprises an anterior part 406 of eye 142. Anterior part 406 comprises iris 206, pupil 208, a cornea 149, an anterior chamber 129 (filled with aqueous humor), a lens 412, and trabecular meshwork 150 of eye 142. (Additional structures in anterior part 406 in the figure are not relevant to the current description, and have been left unlabeled for the sake of simplicity.) Angle 216 of anterior chamber angle 149 is located between cornea 149 and iris 206 and contains trabecular meshwork 150. Sectional view 404 further comprises a partial sectional view of gonioscope 118, showing parts of two facets 119 and distal face 120.

Beam 117 of laser 108 reflects from one of facets 119 of gonioscope 118 and impinges on trabecular meshwork 150 through cornea 149 and anterior chamber 129 (with refraction ignored for the sake of clarity). Due to the low value of cone angle α (less than 3°), beam 117 has a sufficient spot size to deliver laser energy to trabecular meshwork 150 over a sufficient depth for the entire meshwork around the 360° circumference, without the need to re-focus laser 108 during the procedure.

Camera 112 focuses on anterior chamber angle 216 and trabecular meshwork 150 with a sufficient depth of field 402 to capture the entire image 200 (FIG. 2) at a single focal setting of the camera. For example, the depth of field may be more than 1 mm, or more than 2 mm, or more than 3 mm, or more than 4 mm, or even more than 5 mm Depth of field 402 is tied to the size of the blur circle of camera 112, meaning that the depth of field in this case refers to the ability of controller 132 to aim focused treatment beam 117 in the direction of trabecular meshwork 150 even when the trabecular meshwork is not in sharp focus as viewed by operator 136.

Frontal view 414 in FIG. 4B shows trabecular meshwork 150 and anterior chamber angle 216, shown in the XY-plane of Cartesian coordinates 130, indicated in the figure by X- and Y-axes 420. For the sake of this two-dimensional representation, laser beam 117 and depth of field 402 of camera 112 are indicated with their Z-directions flattened and reshaped into a circular shape in the XY-plane. The small cone angle α of beam 117 defines a treatment region 416 extending through trabecular meshwork 150, with a typical laser spot size S of 0.4 mm. As an example, a cone angle α of 1.5° yields a depth D of 3 mm for region 416 with a ±10% change in the spot size over the region. Depth of field 402 for camera 112 may be 2 mm, 3 mm, 4 mm, or more. Having a camera depth of field 402 equal to or larger than the laser depth of focus D assures that, for a focused image on camera 112, beam 117 is also in focus.

Figure 5:
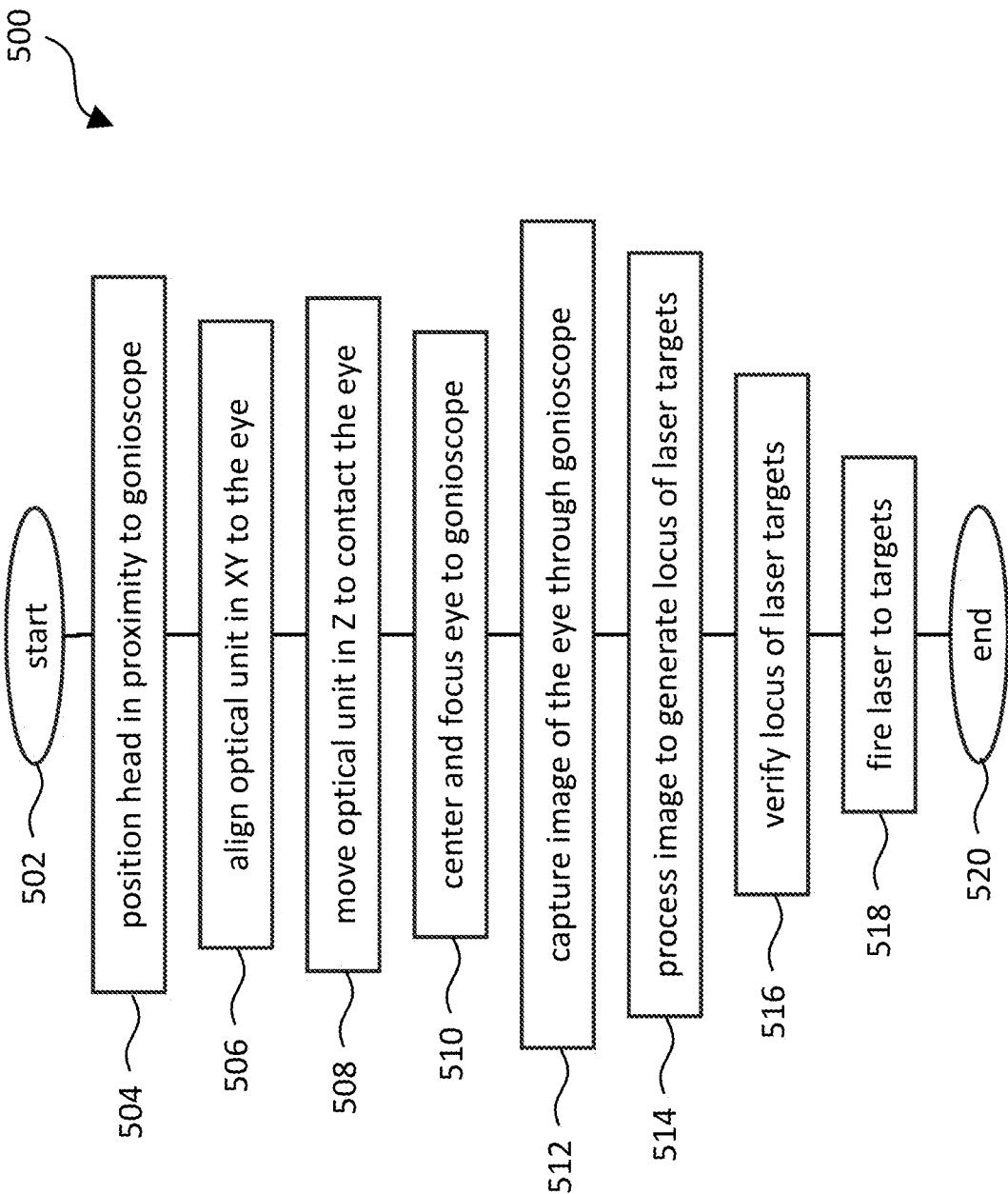
FIG. 5 is a flowchart that schematically illustrates a method for performing an SLT procedure, in accordance with an embodiment of the invention.

FIG. 5 is a flowchart 500 that schematically illustrates a method for performing an SLT procedure using SLT apparatus 100, in accordance with an embodiment of the invention.

The procedure starts in a start step 502. In a head positioning step 504, a patient positions his/her head 140 in proximity of gonioscope 118 (FIG. 1). In an alignment step 506, operator 136 aligns optical unit 102 with eye 142 in the XY-plane. In a Z-movement step 508, operator 136 moves optical unit 102 in the Z-direction so as to contact cornea 149 of eye 142 with distal face 120 of gonioscope 118. In a centering and focusing step 510, operator 136 centers and focuses optical unit 102 to position eye 142 at or near the center of the field of view of camera 112. In an image capture step 512, operator 136 captures with camera 112 an image of eye 142 through gonioscope 118.

In an image processing step 514, controller 132 processes the captured image to define locus 308 of trabecular meshwork 150 (FIG. 3C). In a target verification step 516, operator 136 views locus 308 on trabecular meshwork 150. Optionally, aiming beam 107 is fired around some or all the locus of target points and displayed on monitor 134 to verify correct laser operation. Provided that the locus coincides with the trabecular meshwork, the operator fires laser 108 to impinge on multiple points around the locus in a firing step 518. (If the locus identified by the controller does not coincide with trabecular meshwork 150, operator 136 may command SLT apparatus 100 to return to centering and focusing step 510 or adjust the locus manually.) The SLT procedure ends in an end step 520.

Figure 6:
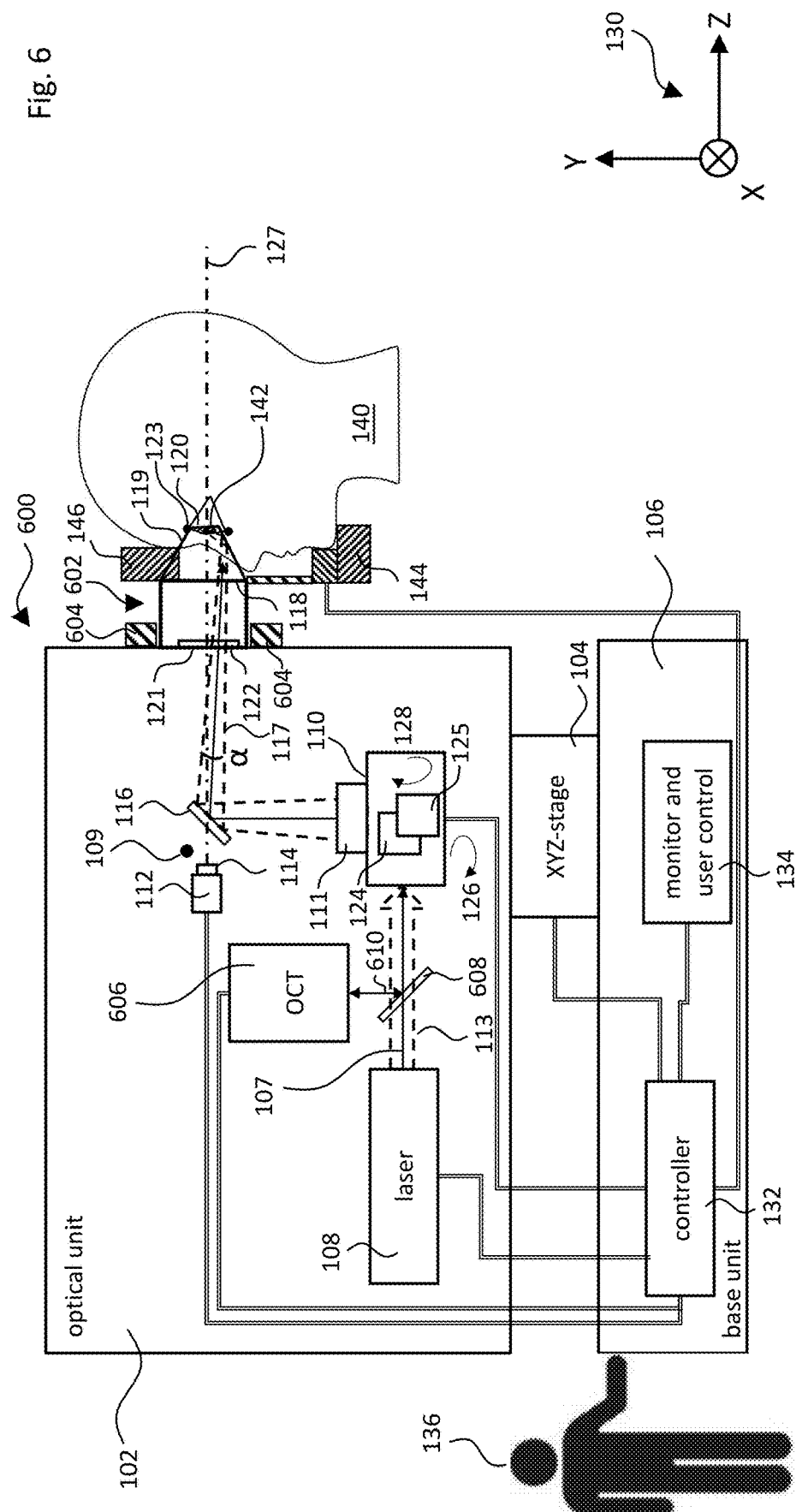
FIG. 6 is a schematic side view of an SLT apparatus, in accordance with an additional embodiment of the invention.

FIG. 6 is a schematic side view of a partially automated SLT apparatus 600, in accordance with an additional embodiment of the invention. Apparatus 600 is similar to apparatus 100 (FIG. 1), and labels from FIG. 1 are used in FIG. 6 for identical or similar items. Apparatus 600 comprises the following items not in apparatus 100: A goniocone assembly 602 and optionally, one or more slit lamps 604 and/or an optical coherence tomography (OCT) unit 606 with a beam combiner 608. Although goniocone assembly 602, slit lamps 604, and OCT unit 606 are shown together in FIG. 6 for the sake of convenience, in practice each of these elements may be incorporated and used separately from and independently of the others.

Goniocone assembly 602 is a fixture that connects between gonioscope 118 and optical unit 102, as further detailed in FIG. 7 hereinbelow. One of slit lamps 604 projects a thin sheet of light (not shown in the figure), reflected by one or more facets 119 of gonioscope 118, to eye 142 at an off-axis angle such as 45°, 30°, 20°, 10°, or 5°. As will be further detailed in FIG. 8 hereinbelow, the reflection of the sheet of light from eye 142 provides an indication of the topography of the eye and assists in aligning treatment beam 117 to trabecular meshwork 150. Alternatively to one sheet of light, multiple sheets of light may be projected by one slit lamp 604 through multiple facets 119 of gonioscope 118 or multiple sheets of light may be projected from multiple slit lamps. These may be utilized for increasing the speed of establishing the topography of eye 142 and aligning treatment beam 117.

OCT unit 606 emits a coherent beam 610, which is aligned optically by beam combiner 608 with aiming beam 107. Utilizing the return of beam 610 from eye 142, OCT unit 606 maps the 3D structure of the eye and transmits it to controller 132. The measured 3D structure provides an additional aid for aligning focused treatment beam 117 to trabecular meshwork 150.

The data from both slit lamp 604 and OCT unit 606 may be displayed to operator 136 for optimal alignment of optical unit 102 around a full 360° range of azimuthal angles.

The embodiments described in FIG. 6 may be utilized both in applications wherein the cone angle α of focused treatment beam 117 is less than 3°, as described hereinabove, and larger than 3°.

Figure 7:
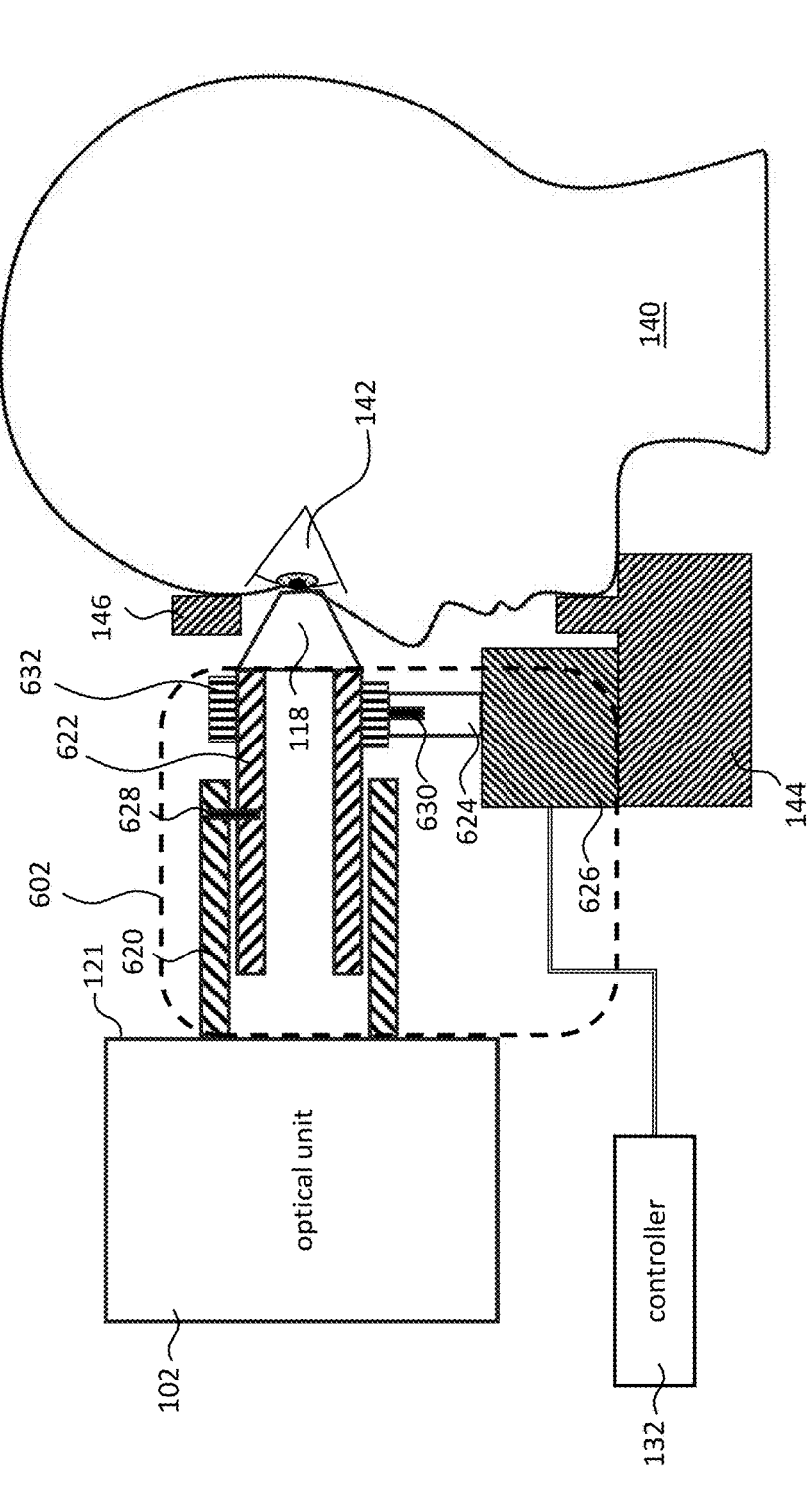
FIG. 7 is a schematic side view of a goniocone assembly used in the apparatus of FIG. 6, in accordance with an embodiment of the invention.

FIG. 7 is a schematic side view of goniocone assembly 602, in accordance with an embodiment of the invention. Labels from FIG. 6 are used in FIG. 7 for identical or similar items.

Goniocone assembly 602 comprises an outer cylinder 620, an inner cylinder 622, a goniocone support 624, an XY-follower 626, an outer lock 628, and an inner lock 630. Goniocone assembly 602 is interfaced to optical unit 102, controller 132, gonioscope 118, and to head 140 via chin rest 144 and via a connection ring 632. Outer cylinder 620 and inner cylinder 622 are hollow, concentric cylinders, with the inner cylinder having freedom of movement in the Z-direction within the outer cylinder. Outer cylinder 620 is attached to proximal face 121 of optical unit 102, and inner cylinder 622 is attached to gonioscope 118. Outer lock 628 locks inner cylinder 622 to outer cylinder 620, and inner lock 630 locks the inner cylinder to XY-follower 626 via support 624. Locks 628 and 630 may comprise any suitable sorts of locking mechanisms, such as pins that are inserted into and retracted from corresponding holes or friction locks. The locking mechanisms of locks 628 and 630 may be activated by, for example, an electric motor or by a pneumatic or hydraulic cylinder. XY-follower 626, attached to chin rest 144, comprises a stage capable of movement in both X- and Y-directions. XY-follower 626 may comprise either an electro-mechanical stage, coupled to controller 132, or alternatively a mechanical stage. The functions of the two alternative stages are detailed hereinbelow. Locks 628 and 630 are coupled to controller 132, which sends commands to lock and unlock the locks. Optionally, inner cylinder 622 may contain a spring or similar element exerting a mild force in the axial (Z) direction for ensuring a constant contact between distal face 120 of gonioscope 118 and cornea 149.

Goniocone assembly 602 enables operator 136 to perform an initial XYZ-alignment between optical unit 102 and eye

142, and then to adjust the alignment of the optical unit during the treatment without inadvertently moving gonioscope 118 into the eye. The SLT procedure, using goniocone assembly 602, starts by following steps 502-508 of flowchart 500 (FIG. 5), while inner cylinder 622 is locked to outer cylinder 620 by outer lock 628, thus fixing the depth of insertion of inner cylinder 622 within outer cylinder 620. (Inner lock 630 is released at this stage.) Up to and including step 508, gonioscope 118 follows the XYZ-alignment of optical unit 102 due to inner cylinder 622 being locked to outer cylinder 620. At the end of step 508, distal face 120 of gonioscope 118 has been brought into contact with cornea 149 of eye 142. After completing step 508, inner cylinder 622, inside connection ring 632, is locked to XY-follower 626 by inner lock 630, thus fixing the axial location (Z-location) of goniocone assembly 602 relative to chin rest 144, and outer lock 628 is released. With this arrangement, the axial location of gonioscope 118 is referenced to eye 142 via chin rest 144 and head 140, and movement of optical unit 102 in the axial (Z) direction will not be conveyed to the gonioscope, thus preventing axial (Z) movement of the optical unit from pushing the gonioscope into the eye.

When XY-follower 626 comprises an electromechanical device, it shifts support 624 and inner cylinder 622, based on commands from controller 132, according to the XY-adjustments of XYZ stage 104 (FIG. 6) that operator 136 performs in step 510 to keep eye 142 centered relative to gonioscope 118. When XY-follower 626 is purely mechanical, it permits support 624 to move freely in the X- and Y-directions but not in the Z-direction. Thus, the XY-movement of optical unit 102 is transmitted to inner cylinder 622 by outer cylinder 620 pushing it in the X- and Y-directions. (In principle, this functionality could be obtained even without XY-follower 626, but the locking of inner cylinder 622 and gonioscope 118 to chin rest 144 would not be assured.) As outer lock 628 has been released, there is no danger that a Z-movement of optical unit 102 will be transmitted to gonioscope 118, and operator 136 may freely adjust the position of the optical unit using a joystick or other control of unit 134. The remaining steps 510-520 of the procedure may then continue without the operator having to hold or manually manipulate the gonioscope.

In alternative embodiments, goniocone assembly 602 may comprise, instead of concentric cylinders, a first and a second mechanical part, with appropriate mechanical coupling for Z-direction adjustment and locking, as explained above. For example, each of the first and second parts may comprise a rail or a rod. The first part is attached to optical unit 102, and the second part is attached to gonioscope 118. The two parts are movable and lockable by first and second locks, similarly to outer cylinder 620 and inner cylinder 622 as described hereinabove.

Figure 8B:
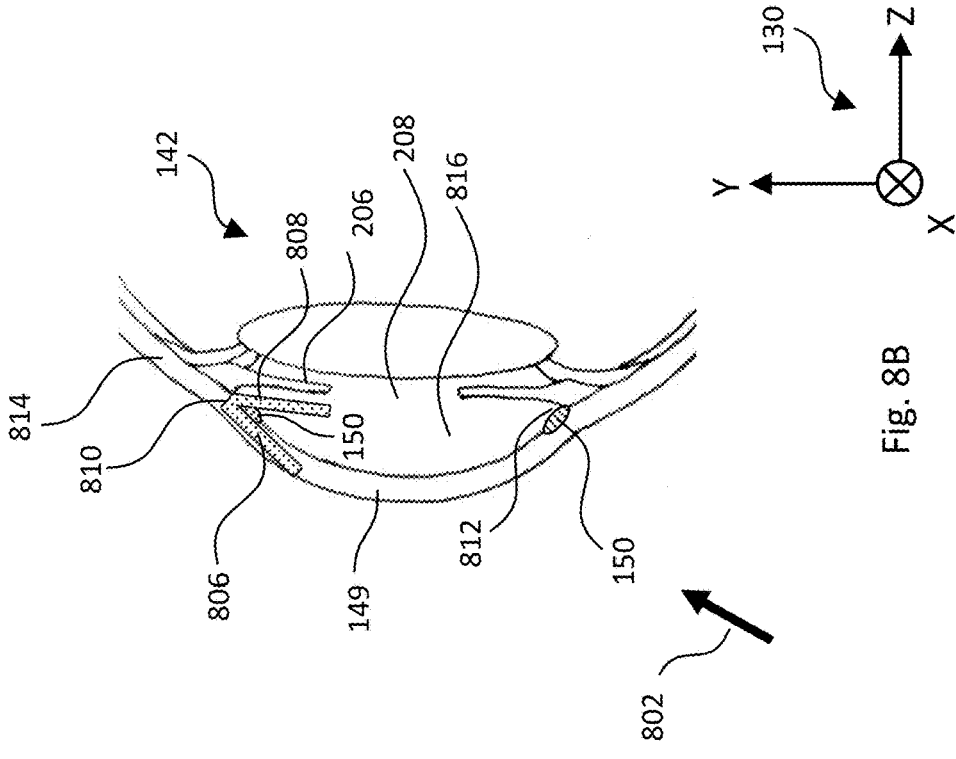
FIGS. 8A and 8B are schematic pictorial and sectional views of an eye, respectively, showing slit lamp illumination used for locating a trabecular meshwork of the eye, in accordance with an embodiment of the invention.
Figure 8A:
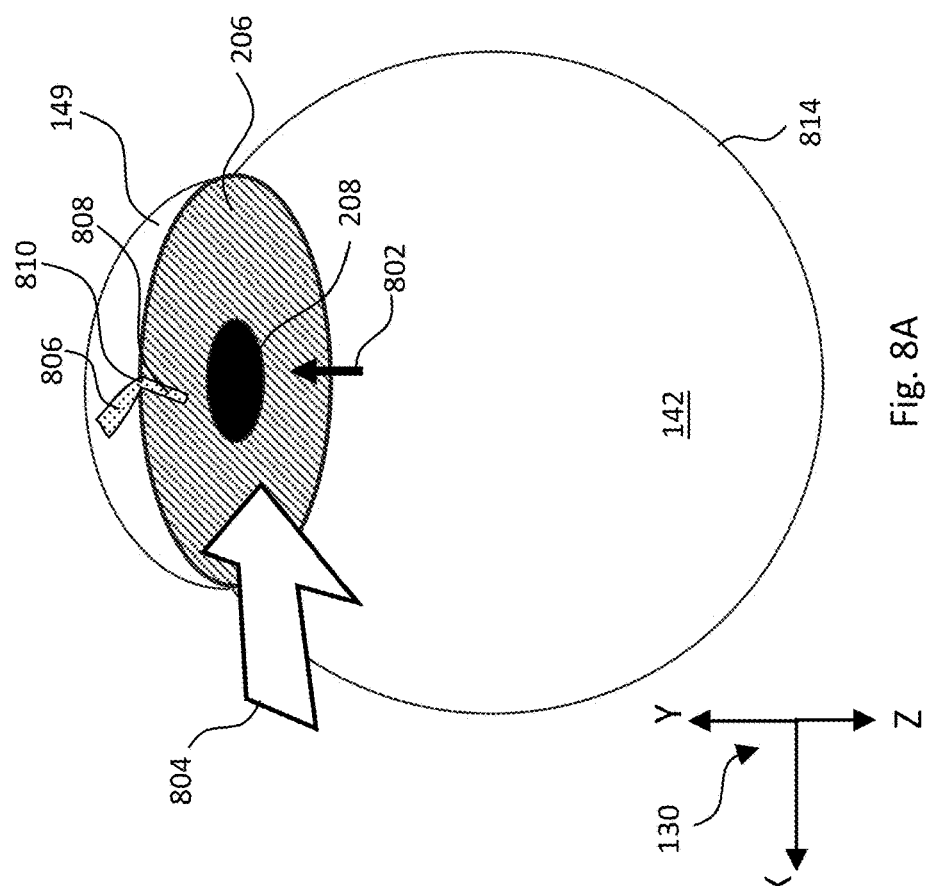

FIGS. 8A and 8B are two schematic views of slit lamp illumination on eye 142 for locating trabecular meshwork 150, in accordance with an embodiment of the invention. Labels from FIGS. 4A and 6 are used in FIGS. 8A and 8B for identical or similar items.

FIG. 8A is a schematic pictorial view of eye 142 as viewed through cornea 149. The direction of view, indicated by an arrow 802 both in FIG. 8A and in FIG. 8B, is in the YZ-plane of Cartesian coordinates 130. (For clarification of the direction of view, the entire eye 142, including a complete sclera 814, is shown in FIG. 8A. In reality, the view through gonioscope 118 comprises iris 206, pupil 208, cornea 149, and only a small portion of a sclera 814 around the iris and cornea.) Eye 142 is illuminated with a thin sheet of light 804 from one of slit lamps 604. Sheet of light 804 reflects from cornea 149 and from iris 206 as two respective elongated patterns 806 and 808. Patterns 806 and 808 meet at an elbow-like bend 810.

FIG. 8B is a sectional view of eye 142 showing patterns 806 and 808 reflected from slit lamp sheet of light 804. Bend 810 is located at an angle 812 of an anterior chamber 816 of eye 142. Angle 812 is the point where the curvature of cornea 149 meets iris 206 of eye 142. Angle 812, in turn, is a landmark that is located within a known offset from trabecular meshwork 150. Alternatively, by observing pattern 806 while moving light sheet 804 along cornea 149, a border 820 (FIG. 8C) of the cornea may be found at the minimum width of pattern 806. The center of trabecular meshwork 150 is located between border 820 and angle 812.

Figure 8C:
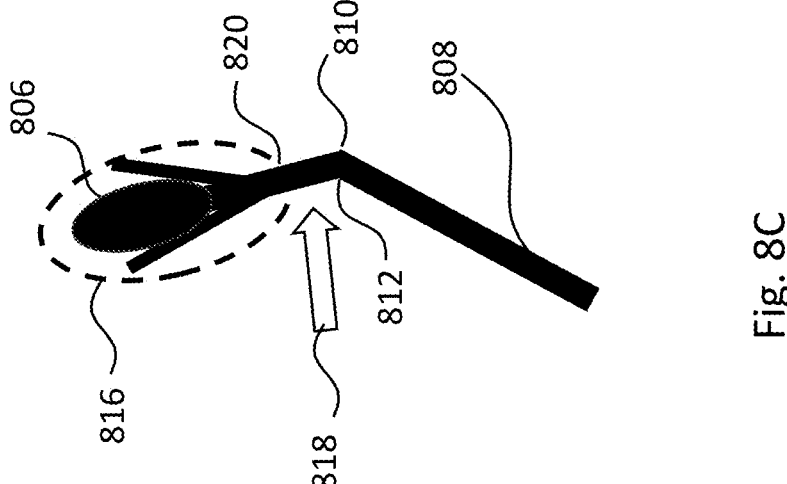
FIG. 8C is a schematic representation of an image captured by a camera of a part of an eye under slit lamp illumination, in accordance with an embodiment of the invention.

FIG. 8C is an example image of patterns 806 and 808, captured by camera 112 in apparatus 600, in accordance with an embodiment of the invention. A portion 816 of cornea 149 is indicated with a dashed line. Controller 132 processes the image to find the location of bend 810, which indicates the location of the angle 812. Controller 132 then finds the location of trabecular meshwork 150, indicated by an arrow 818, at a known offset from the angle 812. Alternatively or additionally, controller 132 processes the image to find border 820 of cornea 149, and then finds the location of trabecular meshwork 150 between the corneal border and angle 812.

Illumination from slit lamps 604 and/or 3D mapping by OCT unit 606 of the structure of eye 142 may be used in centering and focusing step 510 (FIG. 5). While controller 132 uses the image of eye 149 captured by camera 112 for focusing the camera on the eye, it utilizes the symmetry of the slit lamp illumination as well as the identification of the angle 812 for lateral (XY) alignment.

Controller 132 may determine locus 308 (FIG. 3C) of target points on trabecular meshwork 150 in step 514 by using the 3D OCT map of eye 149 and/or the landmarks indicated by slit lamp illumination, as illustrated in FIGS. 8A-8C hereinabove. Other landmarks of eye 142 known in ophthalmology, such as the ciliary body band, Schwalbe's line, scleral spur, or edge of iris 206, with known offsets from trabecular meshwork 150, may additionally be utilized in the target point determination.

Once locus 308 has been verified in step 516, controller 132 may track the eye while firing laser 108 in step 518, based on pattern recognition of landmarks or the image of pupil 208 and/or iris 206 captured by camera 112.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for medical treatment, comprising:
    a gonioscope having a distal face, which is configured for placement in proximity to an eye of a patient, a proximal face opposite the distal face, and multiple facets extending between the distal and proximal faces;
    a laser configured to generate a beam of optical radiation;
    a scanner, which is configured to direct the beam through the proximal face of the gonioscope so that the beam reflects from a facet of the gonioscope into an anterior chamber of the eye;

at least one slit lamp configured to project at least one sheet of light into the eye through the gonioscope;
    a camera configured to capture, through the gonioscope, an image of an illumination pattern cast on the eye by the at least one sheet of light; and
    a processor, which is configured to process the image of the illumination pattern so as to identify a location of an anatomical structure in the eye, to select one or more targets in the eye based on the identified location, and to control the scanner so that the beam impinges on the one or more targets.

2. The apparatus according to claim 1, wherein the processor is configured to identify the location of a trabecular meshwork in the eye based on the image of the illumination pattern.

3. The apparatus according to claim 2, wherein the processor is configured to select the one or more targets so that the beam irradiates the trabecular meshwork in the eye.

4. The apparatus according to claim 1, wherein the at least one slit lamp is configured to project the at least one sheet of light onto a cornea and an iris of the eye, and wherein the processor is configured to process the image of the illumination pattern so as to identify an angle of an anterior chamber of the eye.

5. The apparatus according to claim 4, wherein the processor is configured to identify the angle of the anterior chamber by finding a bend in the illumination pattern.

6. The apparatus according to claim 1, and comprising an optical coherence tomography (OCT) unit coupled to the processor and configured to map a three-dimensional (3D) structure of the eye, wherein the processor is configured to select the one or target points responsively to the 3D structure.

7. The apparatus according to claim 1, wherein the at least one slit lamp is configured to project multiple sheets of light into the eye through respective facets of the gonioscope.

8. Apparatus for medical treatment, comprising:
    a gonioscope having a distal face, which is configured for placement in proximity to an eye of a patient, and a proximal face opposite the distal face;
    an optical unit movable axially and transversely relative to an optical axis of the eye; and
    a fixture for coupling the gonioscope to the optical unit while aligning the optical unit with the eye through the gonioscope, the fixture comprising:
        a mechanical stage configured to move transversely to the optical axis of the eye so as to follow transverse movement of the optical unit;
        a first part attached to the optical unit;
        a second part attached to the gonioscope and configured to move axially relative to the first part;
        a first lock configured to lock and unlock the second part to the first part; and
        a second lock configured to lock and unlock the second part to the mechanical stage.

9. The apparatus according to claim 8, wherein the first and second parts comprise concentric cylinders of different, respective diameters.

10. The apparatus according to claim 9, wherein the first lock fixes a depth of insertion of one of the concentric cylinders within the other of the concentric cylinders.

11. The apparatus according to claim 8, wherein the second lock fixes an axial location of the second part of the fixture relative to the eye of the patient.

12. The apparatus according to claim 8, wherein the first and second locks comprise respective pins that are inserted into and retracted from respective holes.

13. The apparatus according to claim 8, wherein alignment of the optical unit with the eye comprises an axial alignment step with the first lock closed and the second lock open, followed by a transverse alignment step with the first lock open and the second lock closed.

14. The apparatus according to claim 8, wherein the optical unit comprises a camera configured to capture an image of the eye through the proximal face of the gonioscope.

15. The apparatus according to claim 8, wherein the optical unit comprises a laser configured to irradiate the eye with a beam of radiation directed through the gonioscope.

16. The apparatus according to claim 15, wherein the optical unit comprises a scanner, which is configured to direct the beam through the proximal face of the gonioscope so that the beam reflects from a facet of the gonioscope into an anterior chamber of the eye to impinge on tissue in the anterior chamber.

17. The apparatus according to claim 8, and comprising a chin rest, to which the mechanical stage is attached so as to shift the fixture transversely relative to the eye while a chin of the patient rests on the chin rest.

18. A method for medical treatment, the method comprising:

positioning a distal face of a gonioscope in proximity to an eye of a patient;

projecting at least one sheet of light into the eye through the gonioscope;

capturing through the gonioscope an image of an illumination pattern cast on the eye by the at least one sheet of light;

processing the image of the illumination pattern so as to identify a location of an anatomical structure in the eye;

selecting one or more targets in the eye based on the identified location; and directing a beam of optical radiation emitted by a laser through a proximal face of the gonioscope so that the beam impinges on the one or more targets.

19. The method according to claim 18, wherein identifying the location comprises finding the location of a trabecular meshwork in the eye based on the illumination pattern.

20. The method according to claim 19, wherein selecting the one or more targets comprises choosing the one or more targets so that the beam irradiates the trabecular meshwork in the eye.

21. The method according to claim 18, wherein projecting the at least one sheet of light comprises illuminating a cornea and an iris of the eye with the at least one sheet of light, and wherein processing the image comprises identifying an angle of an anterior chamber of the eye.

22. The method according to claim 21, wherein identifying the angle of the anterior chamber comprises finding a bend in the illumination pattern.

23. The method according to claim 18, and comprising mapping a three-dimensional (3D) structure of the eye using optical coherence tomography (OCT), wherein selecting the one or target points comprises identifying the one or more target points responsively to the 3D structure.

24. A method according to claim 18, wherein projecting at least one sheet of light comprises projecting multiple sheets of light into the eye through respective facets of the gonioscope.

25. A method for medical treatment, the method comprising:

positioning a distal face of a gonioscope in proximity to an eye of a patient;

coupling the gonioscope to an optical unit, which is movable axially and transversely relative to an optical axis of the eye, using a fixture comprising:

a mechanical stage configured to move transversely to the optical axis of the eye so as to follow transverse movement of the optical unit;

a first part attached to the optical unit;

a second part attached to the gonioscope and configured to move axially relative to the first part;

a first lock configured to lock and unlock the second part to the first part; and a second lock configured to lock and unlock the second part to the mechanical stage; and aligning the optical unit with the eye through the gonioscope using the fixture.

26. The method according to claim 25, wherein the first and second parts comprise two concentric cylinders of different, respective diameters.

27. The method according to claim 26, wherein aligning the optical unit comprises closing the first lock to fix a depth of insertion of one of the concentric cylinders within the other of the concentric cylinders.

28. The method according to claim 25, wherein aligning the optical unit comprises closing the second lock to fix an axial location of the second part of the fixture relative to the eye of the patient.

29. The method according to claim 25, wherein aligning the optical unit comprises an axial alignment step with the first lock closed and the second lock open, followed by a transverse alignment step with the first lock open and the second lock closed.

30. The method according to claim 25, wherein the first and second locks comprise respective pins that are inserted into and retracted from respective holes.

31. The method according to claim 25, and comprising capturing, using the optical unit, an image of an anterior chamber of the eye through the proximal face of the gonioscope.

32. The method according to claim 25, and comprising irradiating the eye with a beam of laser radiation directed from the optical unit through the gonioscope.

33. The method according to claim 32, wherein irradiating the eye comprises directing the beam through the proximal face of the gonioscope so that the beam reflects from a facet of the gonioscope into an anterior chamber of the eye to impinge on tissue in the anterior chamber.

34. The method according to claim 25, wherein coupling the gonioscope comprises attaching the mechanical stage to a chin rest, and wherein aligning the optical unit comprises shifting the fixture transversely relative to the eye by movement of the mechanical stage while a chin of the patient rests on the chin rest.

* * * * *